United States Patent [19]
Chang et al.

[11] Patent Number: 5,573,532
[45] Date of Patent: Nov. 12, 1996

[54] CRYOGENIC SURGICAL INSTRUMENT AND METHOD OF MANUFACTURING THE SAME

[75] Inventors: Zhao H. Chang, Poolesville, Md.; John Baust, Candor, N.Y.; J. J. Finkelstein, Bethesda, Md.

[73] Assignee: Cryomedical Sciences, Inc., Rockville, Md.

[21] Appl. No.: 372,121

[22] Filed: Jan. 13, 1995

[51] Int. Cl.⁶ .................................................. A61B 17/36
[52] U.S. Cl. ........................... 606/26; 228/221; 606/23
[58] Field of Search ........................... 228/221; 606/22, 606/23, 26

[56] References Cited

U.S. PATENT DOCUMENTS

| | | | |
|---|---|---|---|
| Re. 27,733 | 8/1973 | Bereza | 228/221 X |
| 2,800,711 | 7/1957 | Oliphant et al. | 228/221 |
| 2,822,609 | 2/1958 | Horvitz | 228/220 X |
| 2,943,181 | 6/1960 | Gunow et al. | 228/221 X |
| 3,512,245 | 5/1970 | Hermann | 228/221 X |
| 4,072,152 | 2/1978 | Linehan | 606/22 |
| 4,081,121 | 3/1978 | Picard | 228/221 X |
| 4,118,542 | 10/1978 | Walter | 228/217 X |
| 4,146,030 | 3/1979 | Holroyd | 606/26 |
| 4,401,254 | 8/1983 | Tramontini | 228/217 |
| 4,804,128 | 2/1989 | Brittin | 228/221 X |
| 4,997,124 | 3/1991 | Kitabatake et al. | 228/221 X |
| 5,078,713 | 1/1992 | Varney | 606/23 |
| 5,108,390 | 4/1992 | Potocky et al. | 606/21 |
| 5,139,496 | 8/1992 | Hed | 606/23 |
| 5,224,943 | 7/1993 | Goddard | 606/22 X |
| 5,445,312 | 8/1995 | Francis | 228/221 |

*Primary Examiner*—Kenneth J. Ramsey
*Attorney, Agent, or Firm*—Sherman and Shalloway

[57] ABSTRACT

A cryogenic surgical instrument and method of manufacturing the same are described. The instrument is a cryosurgical probe having concentrically arranged cryogenic fluid supply and return tubes extending through a concentric handle portion into a closed end probe shaft wherein the handle portion and a substantial length of the probe shaft are evacuated to provide a layer of thermal insulation between the cryogenic fluid supply and return tubes and the exterior of the instrument. All the parts of the probe structure are joined by vacuum brazing method carried out in an evacuated furnace. The method involves assembling the probe parts into sub-assemblies which are vacuum brazed at a temperature of at least about 1000° F. and a vacuum of at least about $1\times10^{-3}$ Torr. The sub-assemblies are then assembled into the final probe assembly which is likewise vacuum brazed. The final vacuum brazing step simultaneously draws a vacuum within the handle portion and probe shaft through small gaps between the junctions of the sub-assemblies or via a heat sealable valve which is sealed by the brazing method thereby maintaining the vacuum within the handle and probe shaft for thermal insulation. The strength and hardness of the probe shaft may be increased by cold-working, particularly by a combination of swaging and shot-peening. Probe shafts of curved configurations may also be formed. Multiple sub-assemblies and final assemblies can be formed at the same time in a vacuum brazing furnace.

26 Claims, 6 Drawing Sheets

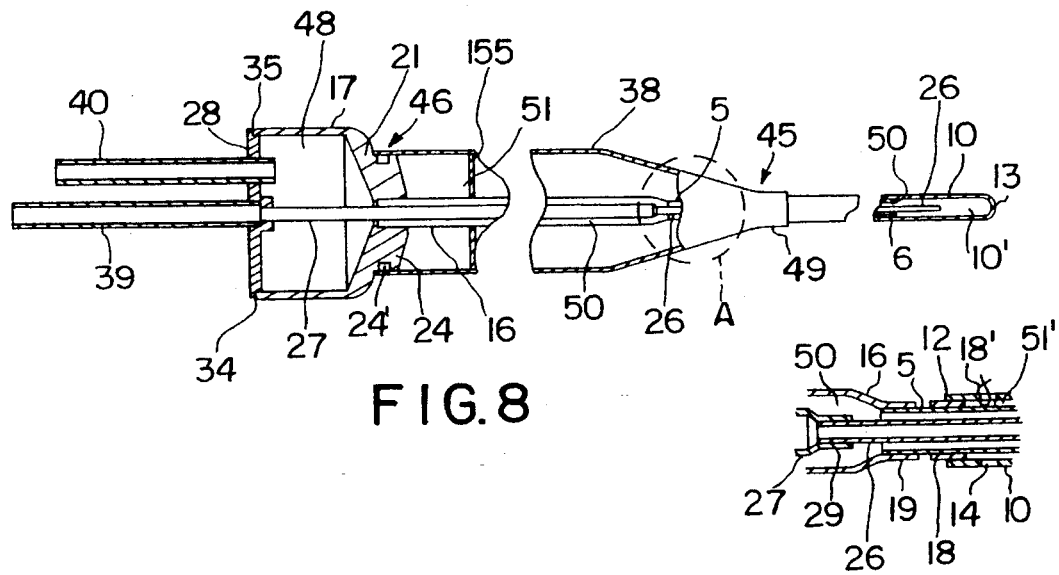
FIG. 8
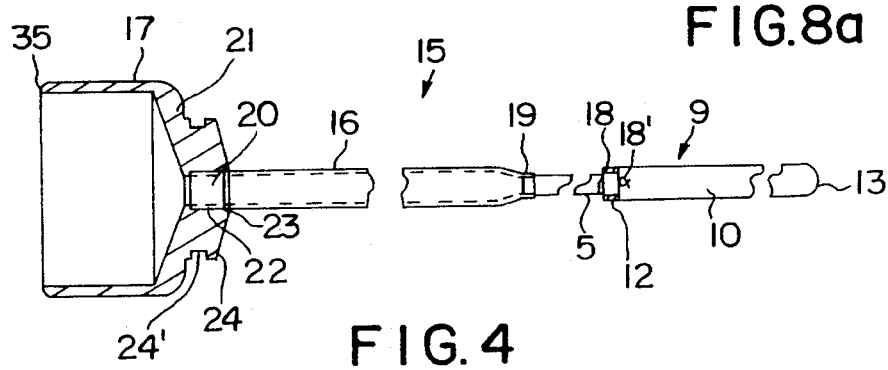
FIG. 8a
FIG. 4
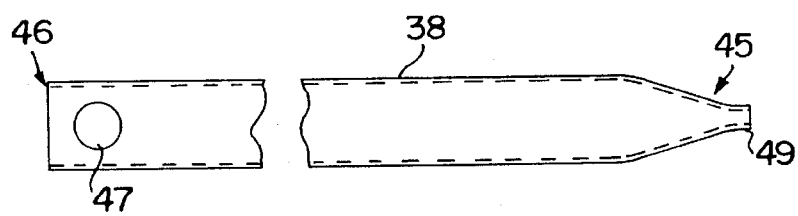
FIG. 7
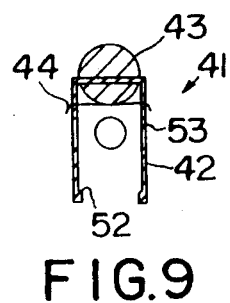
FIG. 9
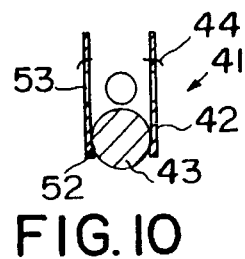
FIG. 10
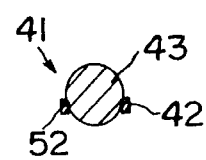
FIG. 11

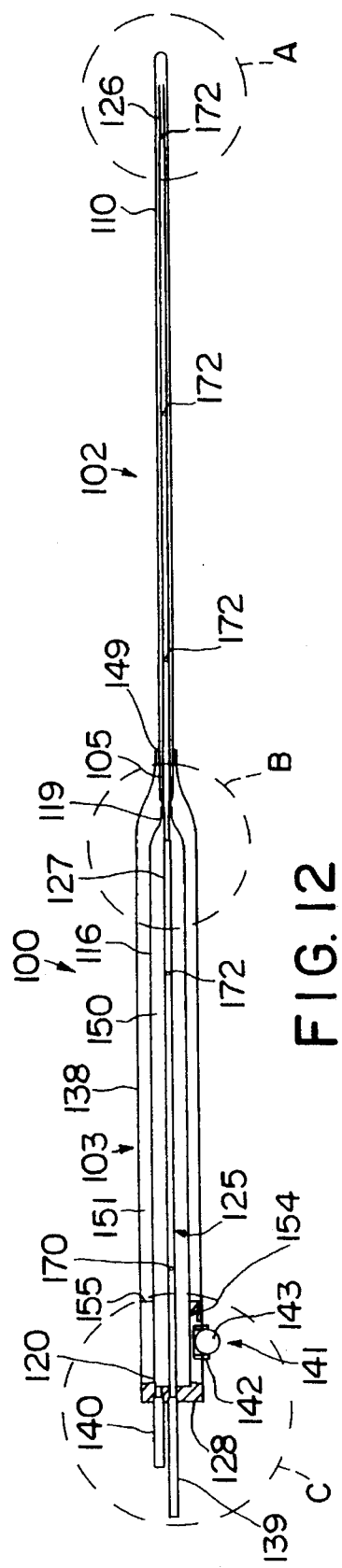
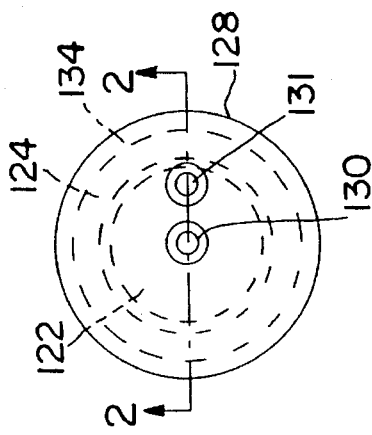
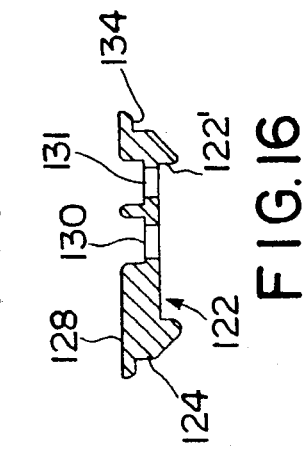
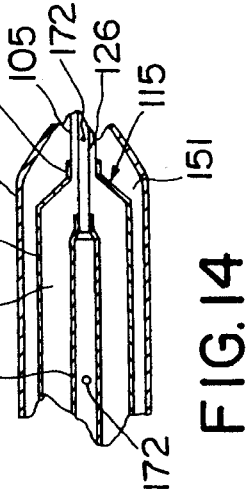
FIG. 12
FIG. 13
FIG. 14
FIG. 15
FIG. 16

CRYOGENIC SURGICAL INSTRUMENT AND METHOD OF MANUFACTURING THE SAME

FIELD OF THE INVENTION

The present invention relates to the field of cryoprobes for use in cryosurgical applications and to the methods by which such probes are made. More particularly, it relates to a cryoprobe having improved properties of thermal insulation, shelf life, and the like, and to a method of manufacture which contributes to these improved properties and which facilitates economical mass production of precision cryoprobes.

BACKGROUND OF THE INVENTION

Cryosurgery is a well established surgical method which is useful in the treatment of many conditions and which involves the application of extreme cold to tissues to effect freezing of the tissues. Cooling and defrosting in such a method is achieved by a variety of methods. Considering only probe-type instruments, as opposed to direct topical application of a cryogen, cryosurgery may include the introduction of a low boiling point refrigerant into a closed probe tip, gas expansion utilizing the Joule-Thompson effect, employing the latent heat of vaporization such as with freon, precooled gases and liquids, or thermoelectric cooling.

A preferred form of cryosurgery employs a closed end probe through which a low boiling point refrigerant or a Joule-Thompson expansion fluid is circulated. Such a closed end probe confines the cryogenic fluid within the instrument rather than applying it directly to the tissues being treated. In closed end probes, the cold generated by a cryogenic fluid is confined to the area of the probe tip where heat transfer occurs across the probe tip to the surrounding tissues and forms an ice ball therein.

Prior art probes have generally been manufactured by methods which introduce potential points of weakness or reduce the effectiveness of the devices. For example, common prior methods of construction include press-fitting of parts, soldering and welding, e.g., Tig welding. Press-fitting as in, for example, U.S. Pat. No. 3,439,680 to Thomas, Jr., is inaccurate and prone to leakage which results in wastage of cryogen and potential damage to surrounding healthy tissues. Soldering and welding are labor intensive and require a degree of precision which renders mass production of probes significantly expensive. In addition, soldering and welding introduce compounds, such as fluxes and oxides, which are difficult to remove from the final probe assembly, particularly the tight, confined areas within the probe, and, if left, can cause degradation of the joints and leakage of cryogen. Furthermore., in these prior methods of manufacture, if a vacuum is desired in a probe handle to provide thermal insulation a separate and complicated evacuation procedure is necessary. Maintenance of such vacuums is also subject to the same deficiencies in the joints produced by prior methods.

The inventors herein have devised a probe construction and a method of manufacture therefor which overcomes the deficiencies of the prior art. By employing a vacuum brazing technique, they have produced a cryosurgical probe with improved construction and properties which have heretofore been, at best, difficult to obtain. The construction and method herein also render mass production of probes more economical while permitting the probes thus made to have a high quality and consistent uniformity of construction. In addition, the evacuation of the probe handles and the improved maintenance of that vacuum is more easily and readily obtained and is an integral part of the final assembly steps rather than a separate procedure following manufacture.

At the heart of the present method is the use of vacuum brazing to both draw a vacuum simultaneously on the handle portion and a substantial length of the probe shaft for thermal insulation and to join the individual parts of the probe together. Brazing is an adhesion process in which the base metals being joined are heated to a temperature at which a nonferrous filler, or brazing material, melts and is distributed between the closely fitted surfaces of a joint by capillary attraction. Instead of melting the base materials, as in a welding process, brazing joins the base materials by melting only the brazing material and doing so at temperatures at which a degree of alloying may occur between the base metal and brazing material. The resulting joint is smoother and more uniform and is generally less subject to the effects of stress than welded or soldered joints.

In vacuum brazing, the components, with brazing material pre-positioned at the joint locations, are placed in a furnace and subjected to brazing heat under a vacuum. The use of vacuum eliminates the need for mineral fluxes that are used in welding and soldering and which can leave residual contaminants on the surfaces of the probes. The brazements are then cooled or quenched by appropriate protocols to minimize distortion and produce the required properties in the base and brazing materials. Commercial vacuum brazing is generally accomplished at pressures varying from 0.5 Torr to $10^{-6}$ Torr, depending on the applications. Vacuum brazing has typically been used to fabricate vacuum tubes for electronic devices, as well as bodies of similar and dissimilar metals including stainless steel, super alloys, aluminum alloys, refractory materials and ceramics. The following patents are representative of such brazing methods and processes: U.S. Pat. No. 2,800,711, Oliphant, et al.; U.S. Pat. No. 2,822,609, Horvitz; U.S. Pat. No. 2,943,181, Gunow, et al.; U.S. Pat. No. 3,512,245, Hermann; U.S. Pat. No. 4,081, 121, Picard; U.S. Pat. No. 4,118,542, Walter; U.S. Pat. No. 4,401,254, Tramontini; U.S. Pat. No. 4,804,128, Brittin, and U.S. Pat. No. 27,733, Bereza, the disclosures of which are incorporated herein by reference thereto.

In the construction of cryoprobes, the inventors have found that vacuum brazing provides advantages over other joining means, including soldering, welding, epoxy, or other brazing methods. Although brazing is a known method and has been disclosed in the patent art as a possible alternative for partial construction of cryogenic probes, (for example, Thomas, Jr., U.S. Pat. No. 3,439,680, discloses brazing a stainless steel tip onto the end of a probe and Ritson, et al., U.S. Pat. No. 3,913,581 discloses brazing a thin walled stainless steel tube into a cylindrical body), the present inventors have found no evidence suggesting the use of vacuum brazing in the manner herein described for the complete construction and evacuation of cryoprobes. The present invention has the following advantages over probes manufactured according to prior methods.

As noted, the vacuum brazed cryoprobe of the present invention eliminates the need for separate pumping to evacuate the handle as well as the probe shaft beyond the freezing zone for thermal insulation. A vacuum is drawn on the probe by the vacuum level of the brazing furnace and the handle is then sealed by the continued vacuum brazing. A sufficiently high vacuum level in the probe's vacuum chamber can be obtained by evacuation through loosely pre-positioned brazing joints or through an evacuation valve, e.g. a valve which is activated and itself sealed simultaneously with the brazing. An evacuation valve is preferred and may be necessary when sufficient evacuation paths are not available, such as when each probe component is tightly fitted during the pre-assembly process as described below. Since the vacuum is produced by the furnace which has a high vacuum applied (at most $10^{-3}$ Torr and preferably at most $10^{-5}$ Torr or lower in pressure, i.e. higher vacuum) as well as the high brazing temperature, and since sealing occurs substantially simultaneously, the evacuation is more complete and can provide better thermal insulation than that obtained by other methods. Even higher vacuums may be achieved by incorporation of a getter in the probe body.

Vacuum brazing is a fluxless process and creates more uniform and cleaner joints than either soldering or welding. Because it is fluxless, there are no residual contaminants of flux or oxides to be cleaned out. Such contaminants may present problems in fine probe production since they can affect the quality of the joints as well as potentially degrade the joints thus affecting the vacuum insulation. In addition, the elimination of fluxes and their oxides reduces the oxidation of the probe material and significantly reduces the level of outgassing by the probe material. This reduction of outgassing improves the vacuum level which is attained in the probes, it reduces the level of joint contamination and it increases the shelf life of the probes. Vacuum brazing removes essentially all occluded gases evolved at close fitting brazing interfaces and, because the probe components have been "pre-outgassed" at the high furnace temperatures and vacuum, any outgassing subsequent to probe construction is minimal thus substantially extending the shelf life of the probes of this invention.

The method of this invention permits high volumes of production with consistent and uniform quality since a plurality of probes may be produced with each run of the furnace. The number of probes produced is primarily limited by the capacity of the furnace used. Compared to welding and soldering, vacuum brazing is more efficient and human error is minimized. Every heating and cooling stage is controllable by automatic means ensuring continuity throughout the process. Furthermore, the high volume and economy of production obtained by vacuum brazing justifies the disposability of the probes produced thus reducing the problems of defects which may arise in re-use of probes manufactured by other methods.

In addition, certain properties, such as probe stiffness or flexibility, which are imparted by the vacuum brazing process are more readily altered or adjusted to need simply by changing the process steps. Although flexible cryosurgical probes have been made before, the flexibility of the probe is generally obtained through a complex construction employing materials which may deteriorate under extreme cold and in which the degree of flexibility is not readily altered without a change in the structure of the devices. Such probes are represented by U.S. Pat. No. 5,078,713, Varney; U.S. Pat. No. 5,108,390, Potocky, et al. and U.S. Pat. No. 5,139,496, Hed. Other probes employ materials which, while having the flexibility to be shaped and the stiffness to retain such shapes, are potentially toxic. For example, U.S. Pat. No. 4,072,152 to Linehan discloses an orthopedic cryosurgical apparatus employing probes formed of lead which are placed within the body. Lead is chosen for its flexibility. However, the annealing effect of the vacuum brazing process of the present invention has the advantage of providing a method whereby the flexibility or stiffness of more common construction materials, such as stainless steel, can be tailored to the point where they can be easily bent or shaped while retaining the desired flow characteristics of the cryogenic fluid. Furthermore, the process allows probes to be pre-shaped then set to retain that shape.

In addition, vacuum brazing produces probes which are safer to use in a clinical environment since there are fewer joints, fewer contaminants and fewer materials. Furthermore, the alloying and annealing which can take place in vacuum brazing produces hermetic joints which are stress free and can better withstand the drastic thermal shocks encountered in cryosurgery. The joints also have a higher ductility and, since they may be substantially all internal rather than external as with welded joints, there is less exposure of joint areas to patient contact.

While the application of the vacuum brazing process as described herein is broadly applicable to any cryosurgical probe construction, particularly those relying on vacuum insulation, the structure of the preferred embodiments of the probe of this invention also presents advantages over the prior art. Both the structure and the method of manufacture make it easier to effect changes in the freezing chamber during manufacture to produce probes which can generate different sizes and shapes of ice balls. Furthermore, the construction of the preferred probe presents a new design which is slimmer and which permits easier positioning of multiple probes in a limited surgical area. Also, the vacuum brazing process produces probes which are extremely clean internally and externally and which do not suffer from discoloration produced by welding or soldering.

The vacuum brazed cryoprobes of this invention may be advantageously used in the assignee's cryosurgical system employing sub-cooled liquid nitrogen as disclosed in copending application Ser. No. 07/953,279 and U.S. Pat. No. 5,334,181, the disclosures of which are incorporated herein in their entirety by reference thereto. Moreover, the invention vacuum brazed cryoprobes also most advantageously and preferably include a vented cryogen supply tube as described in assignee's recently issued U.S. Pat. No. 5,254,116 and in assignee's copending application Ser. No. 08/137,353, the disclosures of which are incorporated herein in their entireties by reference thereto.

It has been observed, however, in studies carried out by and on behalf of one or more of the present inventors that under some conditions of use and for some parameters the operating performance of the invention vacuum brazed cryoprobes was inferior to that of the assignee's current commercially available 3 millimeter (mm) Tig-welded cryoprobes, which are sold as part of the assignee's AccuProbe® cryosurgical system. For example, the external temperature near the probe tip often ranged from about 20° C. to about 50° C. higher for the vacuum brazed cryoprobe as compared to the Tig-welded cryoprobe. One probable cause for this lowered performance was determined to be the location of the opening of the vacuum valve 41 as shown in FIG. 1 forward of the enlarged return chamber, resulting in an uninsulated, or relatively poorly insulated return chamber. While the lower external surface temperatures are still well below 0° C. and capable of freezing and destroying tissue, it is preferred to operate at as low a temperature as possible, consistent with adequate safety and other economic considerations, to minimize the time required for the surgical procedure.

Accordingly, in a particular aspect of the invention, specific design changes are incorporated in the preferred cryoprobe instrument which have resulted in the desired external temperatures at and near the probe tip as well as minimizing cool down time, liquid nitrogen consumption and other operating parameters. These design changes include, in particular, providing a nozzle at the outlet of the cryogen supply tube, and/or optimizing the vent hole pattern in the cryogen supply tube. In addition, the improved vacuum insulation may be extended to the proximal (rear) end of the handle portion corresponding to the enlarged return chamber.

While one or more of these design modifications may be incorporated into the cryoprobe to achieve maximum operating performance, the overall benefits, as discussed previously, for a vacuum brazed cryoprobe, are not dependent on the incorporation of these additional design features.

SUMMARY AND OBJECTS OF THE INVENTION

It is an object of the present invention to provide a cryogenic surgical probe and a method of manufacturing such a probe whereby the drawbacks and deficiencies of the prior art are overcome.

It is a further object of the present invention to provide such a probe having an evacuated handle and probe shaft portion extending to the freezing tip.

It is a still further object of the present invention to provide a method of manufacturing such a probe wherein evacuation and sealing occur substantially simultaneously with the assembly of the probe.

Still yet another object of this invention is to provide a cryosurgical probe providing improved cool down time, reduced cryogen consumption, and very low external probe tip temperatures.

Another object of the invention is to provide a cryosurgical probe with a flexible but hardenable probe shaft.

It is an even further object of the present invention to provide a method of manufacturing a plurality of cryosurgical probes in a single operation.

Further objects and advantages will become evident from the following disclosure and drawings.

The present invention provides a cryogenic surgical probe comprising a probe shaft portion and a handle portion, the probe shaft portion comprising, in a concentric arrangement, an inner elongated cryogen supply tube, an intermediate elongated cryogen return tube and an outer elongated probe shaft tube wherein the probe shaft tube has a closed distal end and an open proximal end, the return tube terminates proximally of the closed distal end of the probe shaft and the supply tube outlet terminates intermediate the distal ends of the return tube and the probe shaft. The handle portion has a diameter greater than that of the probe shaft portion and comprises, in a concentric arrangement, an inner supply tube extension, an intermediate return tube extension and an outer handle body. The handle portion is generally in longitudinal alignment with the probe shaft portion, the supply tube extension connects to the proximal end of the supply tube, the return tube extension connects to the proximal end of the return tube and the handle body connects to the proximal end of the probe shaft. All the connections are fused by vacuum brazing and the proximal end of the handle portion is closed by an end plate which is vacuum brazed in place.

The present invention also provides a method of manufacturing a cryogenic surgical instrument having an elongated probe shaft portion, an evacuated handle portion and means for connecting the instrument to a supply of cryogenic fluid. The method includes the steps of forming individual parts of the instrument from brazable material, assembling the parts into the cryogenic surgical instrument, and vacuum brazing the assembled parts at a temperature sufficient to melt a brazing filler and under a vacuum sufficient to evacuate the assembled probe and to promote fluxless brazing whereby the parts are fused together to complete the instrument and the probe is simultaneously evacuated and sealed. The brazing temperature, which is dependent primarily on the fluxless brazing material, is usually at least about 1000° F. and the vacuum is usually at least about $1 \times 10^{-3}$ Torr.

The invention further provides a method of manufacturing a cryogenic probe having a distal closed tip and proximal connection means to a supply of cryogenic fluid. According to this aspect, the method includes the steps of providing a first sub-assembly including a cryogenic fluid return tube and a connector tube in linear arrangement and vacuum brazing this first sub-assembly whereby the proximal end of the connector tube is joined to the distal end of the return tube; telescopically positioning an elongated tubular tip member having a closed distal end and an open proximal end, (with vent apertures in the wall of the tubular tip member adjacent the proximal end) over the first sub-assembly whereby the connector tube is fully contained within the tubular tip member and the proximal end of the return tube extends from the proximal end of the tubular tip member and vacuum brazing the tubular tip member to the first sub-assembly whereby a second sub-assembly corresponding to the probe shaft portion is formed; aligning a cryogenic fluid return assembly comprising (1) a substantially cup shaped cryogen chamber having an open proximal end and an apertured base and (2) an extension tube extending axially from the aperture in the base and connectable to the proximal end of the return tube of the first sub-assembly with the longitudinal axis of the second sub-assembly and vacuum brazing the cryogen chamber to the extension tube and vacuum brazing the extension tube to the return tube whereby a third sub-assembly is formed; forming a fourth sub-assembly comprising (1) an end cap adapted to engage and seal the open end of the cryogen chamber and having an inner and an outer surface, a central supply aperture extending from the inner surface to the outer surface and a radially offset return aperture extending from the inner surface to the outer surface, and (2) a cryogenic fluid supply tube extending perpendicularly from the central supply aperture on the inner surface of the cap by vacuum brazing the cap and the supply tube together; and conducting final assembly of the cryogenic probe by (i) inserting the third sub-assembly into a tubular handle body whereby the distal end of the third sub-assembly extends through and beyond the distal end of the handle body with the vent apertures of the elongated tip member being located within the handle body so that the area within the handle body communicates with the area within the probe shaft portion and whereby the proximal end of the handle body engages the base of the cryogen chamber, (ii) inserting the fourth sub-assembly into the third sub-assembly whereby the cryogenic fluid supply tube extends telescopically into the cryogenic fluid return tube and the end cap engages and closes the proximal end of the cryogen chamber, and vacuum brazing the cryogenic probe to join the third and fourth sub-assemblies to the handle body. During vacuum brazing in the final assembly, the handle body and the probe portion are evacuated via the vent apertures and the loosely fitted brazing joints between the third and forth sub-assemblies. Alternatively, where the third and forth sub-assemblies are tightly fitted, a thermally activated valve may be provided in a wall of the tubular handle body and evacuation occurs via the valve which is sealed to maintain a vacuum in the handle body and the probe shaft upon and following completion of brazing.

The present invention further provides an improvement in a cryogenic probe of the type including an elongated handle portion, a probe shaft portion extending from one end of the handle portion and having a closed tip at the distal end thereof, cryogenic fluid connection means at the other end of the handle portion, cryogenic fluid supply and return tubes within the handle portion and the probe shaft and extending to the probe tip and the cryogenic fluid connection means forming a fluid circuit extending through the handle portion and the probe shaft. The improvement is achieved by vacuum brazing the parts forming the probe whereby the parts are fluid tightly and smoothly joined, such vacuum brazing also simultaneously evacuating the portion of the probe surrounding the cryogenic fluid return tube in the probe shaft portion and in the handle portion, thereby forming vacuum thermal insulation. The vacuum brazing is preferably conducted in an evacuated furnace at a temperature of at least 1000° F. and a vacuum of at least $1 \times 10^{-3}$ Torr in the presence of a brazing alloy, such as silver based alloys, copper based alloys, gold/nickel brazing alloys, etc.

The vacuum brazed cryogenic probe may be provided with a converging or diverging nozzle at the outlet of the supply tube. The preferred supply tube has at least one vent hole, more preferably at least two vent holes, in communication with the vacuum insulated portion of the return tube.

In still another aspect, the present invention provides a method of manufacturing a cryogenic probe having a distal elongated probe shaft portion, a proximal handle portion and concentric cryogen supply and return conduits passing through the handle portion and into and through the probe shaft portion whereby the supply conduit is within and terminates distally of the return conduit. The probe shaft portion includes a first sub-assembly of an elongated tubular probe shaft member having a closed distal end (forming the tip) and an open proximal end and an elongated cryogenic fluid return tube extending telescopically within the tubular probe shaft member; the components of the first sub-assembly are vacuum brazed. A second sub-assembly includes the first (vacuum brazed) sub-assembly and a return tube extension connected to the proximal end of the return tube in axial alignment with the first sub-assembly wherein the return tube extension is vacuum brazed to the return tube. A third sub-assembly includes a cryogen supply tube, a supply tube extension connected to the proximal end of the supply tube in axial alignment therewith and an end cap connected to the proximal end of the supply tube extension; the components of the third sub-assembly are vacuum brazed. An elongated tubular handle body is provided. The handle body and the sub-assemblies are assembled into a final assembly by inserting the second sub-assembly into the handle body whereby the probe portion extends from the distal end of the handle body and the return tube extension is confined within the handle body, inserting the third sub-assembly into the second sub-assembly whereby the supply tube extends telescopically into the return tube, the supply tube extension is confined within the return tube extension and the end cap closes the proximal end of the return tube extension and the proximal end of the handle body, and vacuum brazing the final assembly whereby the distal end of the housing body is fused to the probe portion and the end cap is fused to the proximal ends of the return tube extension and the housing body.

The present invention in still another aspect thereof provides a method for producing a cryogenic probe comprising an elongated handle portion, a tubular probe shaft portion extending from one end of the handle portion and having a closed tip at its distal end, cryogenic fluid connection means at the other end of the handle portion, cryogenic supply and return tubes longitudinally coaxial within the handle portion and the shaft and extending to the probe tip, the handle portion and the shaft defining a space about the cryogenic supply and return tubes with the distal end of the shaft being sealed from this space, and the cryogenic fluid connection means and the cryogenic supply and return tubes forming a fluid circuit extending through the handle portion and the probe shaft. According to this aspect of the invention, the tubular probe shaft member is formable to a desired shape using a tool comprising an elongated body having a channel formed therethrough which is capable of receiving the tubular probe shaft member. The method of forming the tubular shaft to a particular shape comprises the steps of a) placing the tool on the probe shaft, such that the probe shaft is positioned in the channel of the elongated body, b) flowing a cryogenic fluid through the supply and return tubes within the probe shaft to cool the shaft to a cryogenic state, c) holding the probe shaft at the cryogenic state for a period of time of from about 3 to about 5 minutes, d) stopping the flow of cryogenic fluid through the shaft and allowing the shaft to warm, and e) removing the tool from the probe shaft. The probe shaft thereby takes on the shape of the channel and is set to that shape which may be straight or curved.

The strength and rigidity of the probe shaft may be increased by various expedients including, for example, selecting brazing alloys melting below the softening temperature of the brazable material of the probe shaft, increasing probe shaft outside diameter and wall thickness and cold-working surface conditioning including swaging, shot-peening. However, in a particular preferred embodiment, the strength and rigidity of the probe shaft is increased by a combination of swaging followed by shot-peening.

Using any of the methods described herein, a plurality of probes according to this invention may be produced by simultaneously assembling and vacuum brazing large numbers of sub-assemblies and final assemblies in batches wherein the number of assemblies processed in each batch is primarily limited only by the size of the furnace.

BRIEF DESCRIPTION OF THE DRAWINGS

FIG. 4 is a partial longitudinal cross section of a third sub-assembly taken along line 1—1 of FIG. 1.

FIG. 7 is a plan view of an embodiment of a handle body of a cryosurgical probe of the present invention.

FIG. 8 is a partial longitudinal cross section of the assembled probe of FIG. 1 taken along line 1—1 of FIG. 1 illustrating the internal handle assembly.

FIG. 8a is a cross sectional detail view of area A of FIG. 8.

FIG. 9 is a longitudinal cross section of an embodiment of a thermal valve taken along line 9—9 of FIG. 1.

FIG. 10 is a longitudinal cross section of the thermal valve of FIG. 9 after activation thereof.

FIG. 11 is a longitudinal cross section of the thermal valve of FIG. 10 with excess valve body removed.

FIG. 12 is a longitudinal cross section of an alternative embodiment of a cryosurgical probe of this invention.

FIG. 13 is a detail view of area A of FIG. 12.

FIG. 14 is a detail view of area B of FIG. 12.

FIG. 15 is a plan view of the end cap of FIG. 12.

FIG. 16 is a cross section of the end cap of FIG. 15 taken along line 2—2 of FIG. 15.

LISTING OF PARTS

1 & 100 Probe assembly.
2 & 102 Probe shaft portion.
3 & 103 Handle Portion.
4 & 104 First sub-assembly.
5 & 105 Cryogenic fluid return tube.
6 & 106 Connector tube.
7 Proximal end of connector tube.
8 Distal end of cryogenic fluid return tube.
9 & 109 Second sub-assembly.
10 & 110 Probe shaft.
10' & 110' Freezing chamber.
11 & 111 Annular notch.
12 & 112 Open proximal end of probe shaft.
13 & 113 Probe tip.
14 & 114 Vent holes.
15 & 115 Third sub-assembly.
16 & 116 Return tube extension.
17 Chamber body.
18 & 118 Spacer.
18' & 118' Locking Wire.
19 & 119 Distal end of return tube extension.
20 & 120 Proximal end of return tube extension.
21 Chamber wall.
22 Central bore.
23 Central bore chamfer.
24 & 124 Annular shoulder.
24' Annular notch.
25 & 125 Fourth sub-assembly.
26 & 126 Cryogenic fluid supply tube.
27 & 127 Supply tube extension.
28 & 128 End cap.
29 Distal end of supply tube extension.
30 & 130 End cap central bore.
31 & 131 First radial offset end cap bore.
32 Extension wall.
33 Chamfer.
34 & 134 Circumferential shoulder.
35 Circumferential chamfered edge of chamber body.
36 Second radial offset end cap bore.
37 Thermocouple well.
38 & 138 Handle body.
39 & 139 Cryogenic fluid supply connector.
40 & 140 Cryogenic fluid return connector.
41 & 141 Thermally activated valve.
42, 142 & 242 Valve body.
43 & 143 Valve ball.
44 Activation wire.
45 Distal end of handle body.
46 & 146 Proximal end of handle body.
47 Valve hole.
48 Cryogenic fluid return chamber.
49 & 149 Necked end of handle body.
50 & 150 Cryogenic fluid return lumen.
51 & 151 Handle space.
51' & 151' Coaxial lumen.
52, 152 & 252 Valve seat.
53 Valve vent holes.
54 & 154 Getter.
55 V-block support fixture.
56 Multiple aperture block support fixture.
57 Aperture in block 56.
60 Converging nozzle.
61 Diverging nozzle.
70 & 170 Supply tube large vent hole.
72 & 172 Supply tube small hole.
122 Central end cap recess.
122' End cap recess wall.
155 Mesh screen.
156 Valve Ball Dispenser.
157 Valve Ball Channel.
158 Attachment Band.
159 Valve Ball Release.
160 Probe Shaft Straightening Tool.
161 Block.
162 Longitudinal Bore.
163 Probe Cavity.
164 Probe Shaft Channel.
165 Cryogenic Fluid Hose.
243 Valve Body Perimeter Flange.
244 Valve Body Lip.

DETAILED DESCRIPTION OF THE INVENTION

Figure 1:
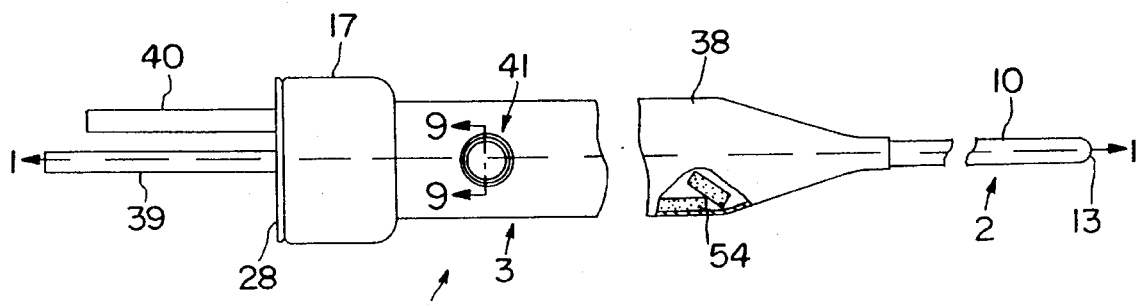
FIG. 1 is a plan view of a first embodiment of a cryosurgical probe of the present invention.

Cryosurgical probe assembly 1, shown in FIG. 1 and in an alternative embodiment 100 in FIG. 12, includes an elongated probe shaft portion 2, and a handle portion 3. Probe shaft portion 2 will typically have a length of from about 4 inches (about 10 cm) to about 12 inches (about 30 cm) depending on the intended end use, a preferred length being from about 6 inches (about 15 cm) to about 8 inches (about 20 cm). The probe shaft 10 of probe shaft portion 2 may typically have an outside diameter of at least about 1.5 mm, preferably at least about 2 mm and especially preferably at least about 3 mm. The upper limit will usually be about 10 mm. While probe shaft portion 2 will usually have a straight configuration with its longitudinal axis coinciding with the longitudinal axis of the handle portion, the probe shaft portion, or at least the distal end thereof, which includes the freezing zone, may also be curved as will be described in further detail below. Still further, for particular applications, the probe shaft portion or at least the freezing tip portion that will come into contact with tissue to be destroyed may be of different configuration than the narrow tubular configuration shown in the drawings, such as well known in the art, for example, an enlarged flattened freezing surface for application to the liver, etc.

Probe assembly 1 is constructed from sub-assemblies 4, 9, 15 and 25 illustrated in FIGS. 2–5, respectively, which are assembled in a substantially longitudinal and concentric arrangement as shown in FIG. 8 and alternatively in FIG. 12. Any suitable material for use in surgical situations and which is brazable may be used for the manufacture of probe 1, for example, stainless steel, ceramic, stainless steel alloys, aluminum alloys, nickel alloys, copper or copper alloys and the like; however, medical grade stainless steel is preferred. Austenitic stainless steel is especially preferred, particularly for the external parts of the instrument which will come into contact with the tissue of a patient to be treated. 304 stainless steel is an austenitic stainless steel and has a microstructure consisting predominantly of polycrystalline austenite.

Figure 2:
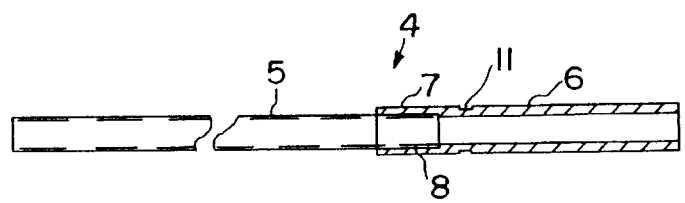
FIG. 2 is a longitudinal cross section of a first sub-assembly taken along line 1—1 of FIG. 1.

First sub-assembly 4, shown in FIG. 2, includes cryogenic fluid return tube 5 and connector tube 6. Cryogenic fluid return tube 5 preferably has an outside diameter which allows it to be inserted into the proximal end 7 of connector tube 6, as shown. A ring of brazing alloy filler (not shown in FIG. 2) is placed over cryogenic fluid return tube 5 and against proximal end 7 of connector tube 6. Proximal end 7 of connector tube 6 may be bored out to a slightly larger inside diameter so as to accommodate distal end 8 of cryogenic fluid return tube 5 and to permit cryogenic fluid return tube 5 and connector tube 6, when assembled, to present a substantially continuous inside diameter. Such a structure presents a substantially smooth conduit for return flow of cryogenic fluid. The length of connector tube 6 may be in the range of, for example, from 0.5 to 0.7 inches or more, while, cryogenic fluid return tube 5 preferably has a length of from 6 to 7 inches for the illustrated embodiment wherein the probe shaft portion is about 7 to 8 inches long. However, other dimensions may be selected depending on the desired final size of probe assembly 1. In the specific embodiments illustrated, the length of first sub-assembly 4 is between 6.5 and 7.5 inches. In an alternative embodiment, first sub-assembly 4 may be fabricated as a single element comprising connector tube 6 as a portion of enlarged outer diameter on the distal end 8 of cryogenic fluid return tube 5. Such an alternative would eliminate one brazing step.

Figure 3:
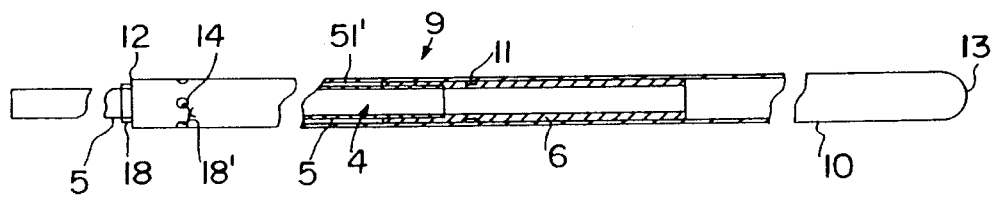
FIG. 3 is a partial longitudinal cross section of a second sub-assembly of the probe of the present invention taken along line 1—1 of FIG. 1.

Second sub-assembly 9, shown in FIG. 3, is formed from first sub-assembly 4 and probe shaft 10 joined by brazing with a fill alloy brazing ring (not shown). First sub-assembly 4 may be provided with annular notch 11 in the outer surface of connector tube 6 to accommodate a fill alloy brazing ring (not shown) when first sub-assembly 4 is inserted into probe shaft 10. Alternatively, a fill alloy brazing ring (not shown) may be placed against proximal end 7 of connector tube 6 prior to insertion of first sub-assembly 4 into probe shaft 10. Probe shaft 10 preferably comprises a tubular body of about 8 inches in length having an open proximal end 12 and a closed distal end (probe tip) 13. Vent holes 14 are provided in probe shaft 10 at a location just distal of open proximal end 12 and their purpose will become evident later in this description.

In assembly of second sub-assembly 9, a fill alloy brazing ring (not shown) is positioned on first sub-assembly 4 as described above. First sub-assembly 4 is then inserted into probe shaft 10, connector tube 6 first, so that a portion, e.g. about 0.6–0.7 inch, of the proximal end of cryogenic fluid return tube 5 extends from open proximal end 12 of probe shaft 10. The space between the outer surface of cryogenic fluid return tube 5 and the inner surface of probe shaft 10 forms coaxial lumen 51'. This distal end of first sub-assembly 4 is positioned from about 1 inch to about 2 inches from the closed probe tip 13 of probe shaft 10. This space forms the freezing chamber 10' (see FIG. 8). Second sub-assembly 9 is then brazed in a manner to be described to join probe shaft 10 and first sub-assembly 4. The size of freezing chamber 10' is easily changed during manufacture by altering the position to which first sub-assembly 4 is inserted into probe shaft 10 during assembly of second sub-assembly 9. Such alteration may also involve providing a shorter or longer first sub-assembly 4 or a shorter or longer probe shaft 10. Thus, freezing chamber 10' may be lengthened or shortened which will, in turn, change the shape and size of the iceball produced when the probe is in use.

Following brazing, second sub-assembly 9 is combined with return tube extension 16, cup-shaped chamber body 17 and spacer 18 to form third sub-assembly 15 shown in FIG. 4. Spacer 18 may, for example, be formed of alumina or other ceramic material and is slidable over the proximal end of cryogenic fluid return tube 5 to be positioned within open proximal end 12 of probe shaft 10 between proximal end 12 and vent holes 14. Proximal end 12 may then be crimped over spacer 18 to hold it in place. However, preferably, spacer 18 has a snug fit within proximal end 12 of probe shaft 10 and a locking wire 18' is threaded through adjacent vent holes 14 to serve as means to ensure that spacer 18 remains at the proximal end 12 of probe shaft 10. FIG. 8a provides an enlarged cross section of the area of proximal end 12 of probe shaft 10 showing the relationship of spacer 18, probe shaft 10, return tube 5 and locking wire 18'. In this manner coaxial lumen 51' is closed off except for communication through vent holes 14. Coaxial lumen 51' thus forms a jacket around cryogenic fluid return tube 5 within probe shaft 10 and is evacuated during the final vacuum brazing and sealing of the fully assembled probe 1 to provide vacuum insulation along at least a substantial length of probe shaft 10. Return tube extension 16 may be about 6 inches long and has a diameter larger than that of cryogenic fluid return tube 5. The distal end 19 of return tube extension 16 is necked down to fit onto the proximal end of cryogenic fluid return tube 5 with a fill alloy brazing ring (not shown) positioned at the juncture thereof.

Chamber body 17 is substantially cup shaped and connects to proximal end 20 of return tube extension 16 to provide an expansion space for cryogenic fluid passing out of probe portion 2 via cryogenic fluid return tube 5 and return tube extension 16. Distal end of chamber body 17 is substantially closed by wall 21 through which central bore 22 is drilled. Central bore 22 is of a diameter to accept proximal end 20 of return tube extension 16. Central bore 22 is preferably provided with a chamfer 23 at its distal end to facilitate insertion of return tube extension 16 and to accept a fill alloy brazing ring (not shown). Surrounding central bore 22 and formed as part of chamber wall 21 is annular shoulder 24 which serves, in the final probe assembly 1, as a plug and support for proximal end 46 of handle body 38 (as shown in FIG. 8). Annular notch 24' in annular shoulder 24 may accept a fill alloy brazing ring (not shown) to join handle body 38 to chamber body 17. Alternatively, joining of handle body 38 to chamber body 17 may be effected by a fill alloy brazing ring (not shown) placed over handle body 38 at the juncture of proximal end 46 of handle body 38 and wall 21 of chamber body 17.

Third sub-assembly 15 is constructed as described with fill alloy brazing rings (not shown) at the junction of cryogenic fluid return tube 5 and return tube extension 16 and at the junction of return tube extension 16 and chamber body 17, preferably in bore chamfer 23. Third sub-assembly 15 is then subjected to appropriate brazing conditions for the particular fill alloy and structural materials. Handle body 38 may also be assembled as part of third sub-assembly 15 at this time.

Figure 5:
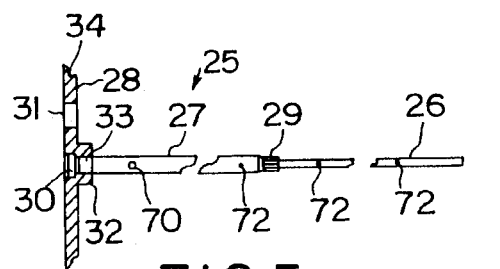
FIG. 5 is a longitudinal cross section of a fourth sub-assembly taken along line 1—1 of FIG. 1.

Fourth sub-assembly 25 is shown in FIG. 5 and includes cryogenic fluid supply tube 26, supply tube extension 27 and end cap 28. All parts are preferably fabricated from the same material as the rest of probe assembly 1. Cryogenic fluid supply tube 26 may be, for example, from about 8 to about 9 inches long and with a diameter to fit concentrically within cryogenic fluid return tube 5 so as to provide a cryogenic fluid return lumen 50 (see FIG. 8) between the inner surface of cryogenic fluid return tube 5 and the outer surface of cryogenic fluid supply tube 26. Supply tube extension 27 may be about 6 inches long and is slightly larger in diameter than cryogenic fluid supply tube 26 and has its distal end 29 necked down to fit securely over the proximal end of cryogenic fluid supply tube 26. Similarly to cryogenic fluid supply tube 26, the diameter of supply tube extension 27 is such as to fit concentrically within return tube extension 16 so as to continue cryogenic fluid return lumen 50 therebetween.

For optimum performance, as previously described in assignee's U.S. Pat. No. 5,254,116 and copending application Ser. No. 08/137,353, the disclosures of which are incorporated herein in their entirety by reference thereto, one or more vent holes are provided along the length of the supply tube, upstream of the connector tube and supply tube outlet (i.e. in the vacuum insulated region), to allow fluid communication between the inflowing liquid cryogen refrigerant and the outflowing or exhaust refrigerant in the cryogenic fluid return lumen. For example, one relatively large diameter vent hole 70 in supply tube extension 27 and several, e.g. 3, relatively smaller diameter vent holes 72 in supply tube parts 26 and 27 are shown in FIG. 5. The larger supply tube vent hole 70 is preferably positioned along supply tube extension 27 so as to be located within the enlarged cryogenic fluid return chamber 48 upon insertion of fourth sub-assembly 25 into third sub-assembly 15.

Figure 6:
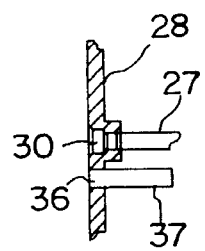
FIG. 6 is an alternative embodiment of the fourth sub-assembly of FIG. 5.

End cap 28 is a circular plate having a central bore 30 and a first radially offset bore 31. End cap central bore 30 is surrounded on the inner surface of end cap 28 by extension wall 32 which provides a place for end cap 28 to connect to the proximal end of supply tube extension 27. As with chamber body 17, the inner end of end cap central bore 30 is preferably provided with a chamfer 33 to facilitate insertion of supply tube extension 27 and to accept a fill alloy brazing ring (not shown). End cap 28 has a diameter to fit over and close the open cup of chamber body 17. To facilitate a close fit therewith, the periphery of end cap 28 is provided with a circumferential shoulder 34 which accepts circumferential chamfered edge 35 of chamber body 17. In an alternative embodiment illustrated in FIG. 6, end cap 28 may have a second radially offset bore 36 to which is connected by brazing a short, closed end thermocouple well 37 extending inward. Thermocouple well 37 provides a space in which a thermocouple, or other temperature measuring device, may be placed to monitor the temperature of returning cryogenic fluid. The parts of fourth sub-assembly 25 are assembled and the sub-assembly is brazed in the manner to be described.

Figure 9A:
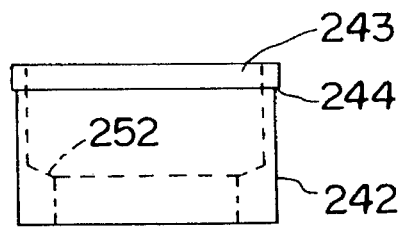
FIG. 9a is a plan view of an alternative embodiment of a thermal valve body which may be used in the manufacture of a cryosurgical probe of the present invention.

Final probe assembly 1 is illustrated in FIG. 8 and is formed by assembling third sub-assembly 15, fourth sub-assembly 25, handle body 38, cryogenic fluid supply connector 39, and cryogenic fluid return connector 40. The embodiment illustrated in FIG. 1 includes optional thermally activated valve 41. An example of one embodiment of valve 41 is illustrated in different stages in FIGS. 9–11 and comprises valve body 42, ball 43 and activation wire 44. An alternative valve body form 242 is illustrated in FIG. 9a for use with the valve ball dispenser 156 of FIGS. 21 and 22 in a manner to be described later. However, as previously noted for less tightly fitted subassemblies, the final evacuation may be affected directly through the narrow spaces left at the junctions between the assembled sub-components and the valve 41 may be omitted.

Handle body 38 is illustrated in FIG. 7 and comprises a tubular body having a length of, for example, from about 6.5 to about 7.0 inches. The diameter of handle body 38 may be from about 0.5 to about 1.0 inch, preferably about 0.6 to 0.75 inch, and has an inside diameter corresponding substantially to the diameter of annular shoulder 24 on chamber wall 21 to fit thereon as shown in FIG. 8. Distal end 45 of handle body 38 is tapered to a size to fit over and engage probe shaft 10 at a location on the distal side of vents 14. In the illustrated embodiment, located in the wall of handle body 38, preferably slightly distally of proximal end 46, is valve hole 47 in which valve body 42 fits and is joined to handle body 38 preferably by vacuum brazing. Also, preferably handle body 38 is provided at this stage with valve body 42 already joined thereto. However, the joining of valve body 42 to handle body 38 at valve hole 47 may take place as part of the final assembly process.

Probe 1 is assembled by inserting fourth sub-assembly 25 into third sub-assembly 15 through chamber body 17. Cryogenic fluid supply tube 26 extends through cryogenic fluid return tube 5 into probe shaft 10 and end cap 28 fits against circumferential chamfered edge 35 of chamber body 17 thereby closing chamber body 17 and forming a cryogenic fluid return chamber 48. This chamber 48 provides a final enlarged area for cryogenic fluid entering chamber 48 from cryogenic fluid return lumen 50 prior to exiting probe assembly 1. The space between cryogenic fluid supply tube 26 and cryogenic fluid return tube 5 and between supply and return tube extensions 27 and 16 forms a cryogenic fluid return lumen 50 which connects freezing chamber 10' and return chamber 48. At the same time, cryogenic fluid supply and return connectors 39 and 40 are positioned in their respective bores 30 and 31 of end cap. Cryogenic fluid supply connector 39 fits into central bore 30 to be coextensive with supply tube extension 27 and cryogenic fluid supply tube 26. Cryogenic fluid return connector 40 fits into first radially offset end cap bore 31 and may extend part way into return chamber 48.

Following assembly of third sub-assembly 15 and fourth sub-assembly 25, screen 155 is placed over return tube extension 16 at a position so as to be distal of valve body 42 when handle body 38 is in place. Handle body 38 is applied over third sub-assembly 15 so that proximal end 46 of handle body 38 fits over annular shoulder 24 and engages chamber wall 21 while probe shaft 10 passes through distal end 45 of handle body 38. The assembly is such that proximal end 12 of probe shaft 10 is located within handle body 38. Handle space 51 is formed within handle body 38 as a lumen between the inner surface of handle body 38 and the outer surface of return tube extension 16 and communicates with coaxial lumen 51' of probe shaft 10 through vents 14. Screen 155 conforms to the shape of handle space 51 and may be a split disc of woven metallic screen material. Alternatively, screen 155 may be placed over return tube extension 16 during the assembly of third sub-assembly 15 prior to installation of chamber body 17. Screen 155 may be omitted but is preferably included as a means to confine getter tablets 54 within the proximal end of handle space 51 to prevent blockage of the connection between handle space 51 and coaxial lumen 51'.

Prior to brazing the final assembly of FIG. 8, in the case where the thermally activated valve 41 is used, the assembly is oriented with valve body 42 uppermost. Since valve body 42 is a tubular structure and is mounted in valve hole 47, it provides access into and out of handle space 51 and, via vents 14, into and out of coaxial lumen 51'. Preferably, valve body 42 has an inner circumferential valve seat 52 at its lower end adjacent handle body 38 and below vent holes 53 in the wall of valve body 42 between the upper and lower ends thereof. Above vent holes 53 is a means to hold activation wire 44. Such a means may be two small holes in the wall of valve body 42 at positions opposite each other and above valve vent holes 53 through which activation wire 44 is threaded, or it may be an opposing pair of slits in the wall of valve body 42 terminating above valve vent holes 53 in which activation wire 44 is laid. Activation wire 44 spans the diameter of valve body 42 and provides a temporary support for ball 43 during the evacuation stage of brazing. Upon substantial completion of evacuation and reaching of brazing temperatures, activation wire 44 melts allowing ball 43 to drop down onto seat 52 below valve vent holes 53. Preferably a fill alloy brazing ring (not shown) is in place on seat 52 and seals ball 43 in place as shown in FIG. 10. Following brazing, the excess amount of valve body 42 above seat 52 and ball 43 is preferably removed as shown in FIG. 11. Preferably, activation wire 44 is a material which melts at or just below brazing temperatures. Any material having this characteristic may be used but a standard brazing wire having a thickness of about 0.005 inch and melting at a temperature of at least about 1000° F., preferably at least about 1300° F. such at least about 1500° F., is particularly preferred.

Valve body 42 also provides a conduit by which a getter 54 is introduced into handle space 51. Preferably getter 54 is compressed in the form of a pill having a size to fit through valve body 41. Getter material appropriate to the materials being brazed is used, for example, ST 707 in pill form, available from SAES Pure Gas, Inc.

In an alternative final assembly, getter 54 is introduced into handle space through valve hole 47 and valve body 242, shown in FIG. 9a, is placed in valve hole 47 with a fill alloy brazing ring (not shown) positioned on valve body 242 so as to be between the outer surface of handle body 38 and valve body perimeter flange 243 under valve body lip 244. In this manner, upon reaching brazing temperature in the furnace, valve body 242 will be brazed to handle body 38 so that only perimeter flange 243 is outside of handle body 38.

Figure 21:
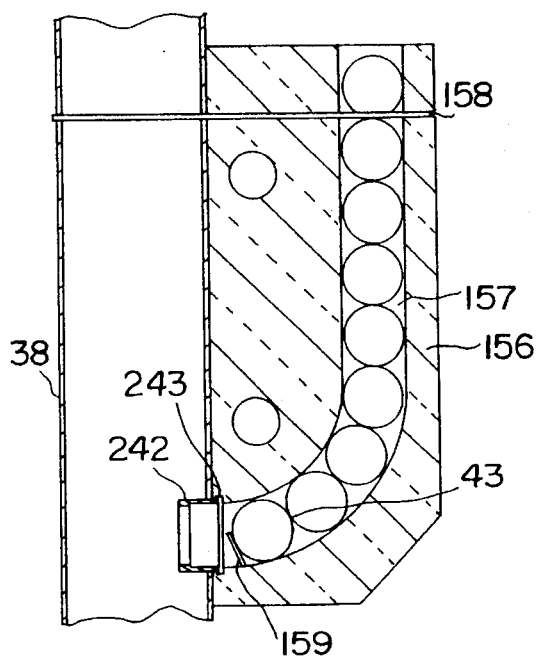
FIG. 21 is a cross sectional view of an apparatus for use in an alternative embodiment for introducing a valve ball into a valve body prior to activation.
Figure 22:
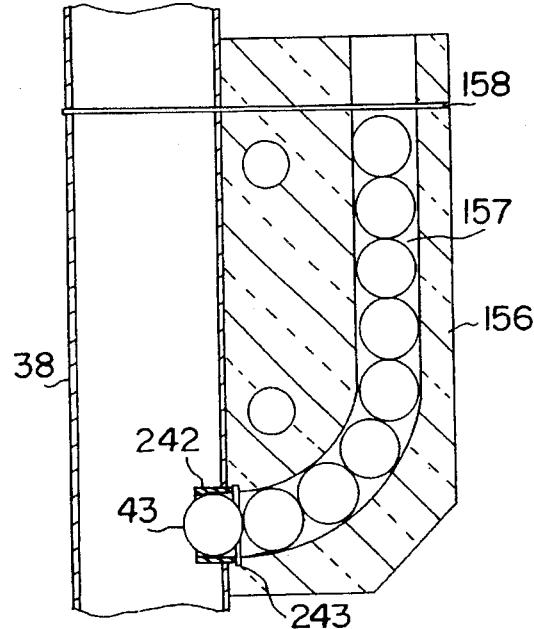
FIG. 22 is a cross sectional view of the apparatus of FIG. 21 following activation.

When alternative valve body 242 is used in the assembly of probes according to this invention, valve ball dispenser 156, shown in FIGS. 21 and 22, is used to introduce valve ball 43 at the correct moment into valve body 242 to seal to valve seat 252 within valve body 242. Valve ball dispenser 156 comprises a body having a curved valve ball channel 157 within the body wherein channel 157 connects with valve body 242 when dispenser 156 is positioned on handle body 38 as shown in FIGS. 21 and 22. Channel 157 also serves as a vent through which the probe interior is evacuated. Attachment band 158 retains dispenser 156 in place on handle body 38. Valve balls 43 are loaded into channel 157 and are held back away from valve body 242 by valve ball release 159. This element holds valve balls 43 back while handle space 51 and coaxial lumen 51' are evacuated by the furnace vacuum through valve body 242 and channel 157. Upon reaching brazing temperature, valve ball release 159 allows a valve ball 43 to roll forward into valve body 242 where ball 43 is brazed onto valve seat 252 by a fill alloy brazing ring (not shown) which is placed within valve body 242 prior to attachment of valve ball dispenser 156. In this manner, probe handle body 38 and probe shaft 10 are evacuated and then sealed to retain the vacuum therein, thereby providing effective thermal insulation of handle portion 3 and probe portion 2.

Valve ball release 159 may be in the nature of activation wire 44 which melts at the brazing temperature to allow passage of valve ball 43. Alternatively, valve ball release 159 may be a material which softens at brazing temperatures and bends to allow passage of valve ball 43 and then hardens upon reduction of the temperature to again prevent passage of valve balls 43. Such materials may include bi-metals selected to correspond to brazing temperatures or memory materials which can be set to have one shape or position at one temperature and another shape or position at another temperature. In such instances, valve ball release 159 will take a position to block passage of valve balls 43 at temperatures below the brazing temperature and will take a position to allow passage of balls immediately before the brazing temperature is reached so that a valve ball 43 is released and is positioned in valve body 242 when the brazing temperature is reached.

In the embodiments of the invention, wherein a thermally activated valve mechanism is not used or required to achieve the desired vacuum, getter material may still be placed within the handle body portion, such as before assembling handle body 38 to chamber body 17, preferably in conjunction with screen 155.

Various brazing alloys suitable for the conditions of the invention and the materials being brazed may be readily determined by the skilled in the art and any such brazing alloys may be used. Brazing alloy GB 8218, which has a composition of 82% gold and 18% nickel, and is available from Prines and Izant Co., has been successfully used. A further brazing alloy suitable for use herein is NICRO-BRAZ®, a nickel and chromium alloy, which is available from Wall Colmonoy Corporation. The brazing alloy may conveniently be provided as preformed rings of wire having diameters appropriate to their location of use, generally from 0.040 inch to 0.9 inch. The diameter of the wire from which the rings are made is from 0.010 to 0.025 inch, preferably 0.015–0.020 inch.

The method of the invention will be described herein with reference to the particularly preferred material which is medical grade stainless steel. Other base materials or brazing alloys may require different temperatures, pressures, heating and cooling times, etc., which may be readily determined by the product or material specifications or by routine experimentation. Regardless of the materials used the maximum brazing temperature will be no more than the softening or degradation temperature of the particular base material and will be at least the temperature at which the particular brazing material melts. Similarly, the vacuum pressure must be sufficient to effectively, e.g., substantially fully, evacuate the probe assembly and to provide the required atmosphere for fluxless brazing. With regard to heating and cooling rates, they may vary with the materials but should be such as to provide even and thorough heating or cooling of the assemblies being brazed. Cooling rates may also be affected by any annealing or tempering effect which is desired to be produced on the probes being manufactured according to the method.

As previously discussed, one of the unique advantages of vacuum brazing in connection with cryosurgical probes is the ability to control the flexibility of the probe shaft portion to achieve design configurations of the probe shaft in the final product which will be particularly well adapted for specific surgical procedures.

There are no established criteria or guidelines regarding the rigidity or stiffness of the probe shaft in the cryosurgical field. The rigidity of the probe varies depending upon the materials, the structural design, the physical dimensions of the probe and the manufacturing process. The requirement for rigidity also varies depending upon the specific clinical applications and personal preference. The rigidity of the probe shaft is, therefore, a very subjective matter. Nevertheless, it would be beneficial to enhance the rigidity of the probe as close as possible to that of conventional probes, such as the TIG-welded probe, without altering the basic design and to maintain functional aspects of the probe design. Therefore, it is generally necessary to harden the probe shaft portion to fix the configuration into its desired shape and avoid undesired deformation during use. Moreover, in some cases, bending the probe shaft can adversely effect the vacuum insulation, for example, inducing cold spots under specific test conditions.

For instance, when tested in air, bending (as small as 3°) of a 3 millimeter nominal (3.4 mm actual) probe shaft, has been observed to cause the temperature at the bending point to drop to below 0° C. after a short period of freezing. When tested in liver at 37° C., however, the temperature at the bending point was observed to be above 0° C. with a bending angle as large as 15° C. for an extended freezing period of 15 minutes. When tested in water at 17° C., the temperature is uniformly above 0° C. along the shaft regardless of the freezing period and bending angle (up to 30°).

Due to its desirable mechanical properties at cryogenic temperatures, its availability in hypodermic tubing form, and its traditional use in the general medical field, 304 stainless steel material has been used to construct the cryoprobe body according to this invention. The material 304 stainless steel falls into the category of austenitic stainless steel and has a microstructure consisting predominantly of polycrystalline austenite. However, it cannot be strengthened by heat treatment such as quenching to form martensite or by precipitation hardening. Typically, strengthening of austenitic stainless steel is accomplished by cold working or solid solution treating. Cold working typically refers to work done on the steel below the thermal critical range and usually at ambient temperature. Common operations include cold rolling, cold pressing, cold drawing, cold extrusion, twisting and swaging, etc. By plastic deformation of the material taking it beyond its yield point, 304 stainless steel typically becomes harder and stronger. Cold working generally improves the yield and tensile strengths. Some of the less stable structural domains may actually undergo a phase transformation and create a martensite phase during cold working. Frequently, 304 stainless-steel material can also be hardened by the application of certain surface-hardening and modification techniques such as gas (or plasma) carburizing, gas carbonitriding, ion implantation and coating (vapor deposition) etc. These solution-treating techniques, however, will simultaneously alter the surface composition of the material. Ideally, the same 304 stainless-steel material should be used for the construction of the entire cryoprobe body or at least the external surface of the probe body which will be in contact with the patient. In order to reduce or eliminate surface composition alteration, the following optional treatments may be performed.

a) Strengthening of the $LN_2$ Return Tube: While it is preferred that the outer shell of the probe shaft will be made from 304 stainless steel, the $LN_2$ return tube can be substituted with a heat-treatable steel such as martensitic stainless steel (e.g. 416) or martensitic-grade, precipitation-hardening stainless steel (e.g. 17.4 PH and 15–5 PH). A fully hardened return tube should substantially improve the rigidity of the probe shaft portion. To gain a fully hardened state, however, an additional heat-treatment process may last several hours or longer. The elongation of the tube, as a result of the martensite phase transformation, coupled with the uneven contraction caused by the cooling process may severely deform the probe shaft in a partially hardened or fully hardened condition which might make it more difficult to straighten than when in a relatively soft, annealed state (for the same reason, the use of martensitic stainless steel for the outer shell of the probe shaft will not generally be the best choice). The selection of brazing materials with relatively low melting temperatures, such as silver- or copper-based alloys, in combination with selection of base materials with relatively high recrystallization and annealing temperatures as well as high strength at a partially annealed or fully annealed state, such as Inconel 600 or 625 or Nitronic 50, may alleviate the problem to a certain extent. The application of materials of such kind together with a low brazing temperature in the neighborhood of 1300° F. and a shortened brazing cycle (possibly with thermal shielding of the probe shaft during the brazing process) is one specific solution.

b) Design Modification: The strength of the probe shaft can also be increased by increasing the outer diameter of the return tube (O.D. only). However, for the preferred embodiment of a probe shaft having an overall diameter of 3.4 mm or smaller, the outer diameter of the return tube can only be increased within its structural limitations. This approach, therefore, has limited potential for a 3.4 mm cryoprobe and is preferably used in combination with other strengthening techniques.

c) Process Modification: For a brazing process using gold-nickel brazing alloy and a duration of 20 minutes brazing at approximately 1850° F., the material 304 stainless steel will be fully annealed. Austenitic stainless steel begins to recrystallize at approximately 1300° F. Subjecting 304 stainless steel to any temperature above this for an extended period will reduce the extent of crystal (grain) distortion and thereby reduce or completely remove the hardness of the material that has been developed solely by cold working the raw materials. By changing to a lower melting silver- or copper-based alloy, the brazing temperature can be reduced to approximately 1300° F. or lower. At this temperature, 304 stainless steel will be only partially annealed within a short period. If the probe shaft is simultaneously shielded from the heat with either a thermal-insulating ceramic cover or a vacuum chamber, the annealing effect can be further reduced. Studies conducted at multiple locations by or for the present inventors indicate that the use of low-temperature brazing alloys and thermal shielding are feasible from a technical point of view.

d) Surface Conditioning (shot peening): The surface of the probe shaft can also be "cold-worked" by bombarding the outer surface with a stream of blasting media such as metal or glass beads, a process often referred to as shot peening. The degree of "cold-working" depends upon the peening intensity which, in turn, is a function of the diameter of the media, its density, as well as the velocity at which it strikes the surface. In practice, the striking velocity can be changed by varying the air pressure. The shot peening process, however, only hardens a single (or few) layers of atoms on the external surface of the probe shaft.

e) Surface Conditioning (swaging): The swaging process, i.e. cylindrical swaging has the advantage of hardening from the outer shell through the wall thickness and, therefore, potentially affords a much stronger probe shaft than the shot-peening process. The swaging process also has the advantage in that a more uniform diameter of the probe shaft can be more easily attained and avoid shaft diameter variations resulting from the tolerance of raw materials. However, the probe shaft should not be over swaged or under swaged. An under-swaged probe will not create the desired rigidity, while an over-swaged probe will compromise the structural integrity, heat-transfer efficiency and vacuum insulation. Of the many probe-shaft diameters possible after swaging, e.g. 0.118", 0.1195", 0.124", 0.1275", and 0.130", the optimum diameter has been found to be 0.130". This is in contrast to a diameter of 0.132"–0.134" of the probe before swaging. However, even a dimensionally properly swaged probe shaft will be subject to various negative consequences. One predictable negative consequence of the swaging process is the creation of stress risers which are the surface grains pulled apart by the tensile strength. A badly disarrayed surface becomes considerably weakened and vulnerable to mechanical load, fatigue and, more important, becomes susceptible to stress corrosion cracking.

f) Surface Conditioning (Swaging and Shot-Peening): This is a newly discovered process to adjust the flexibility of the probe shaft, namely the combination of swaging and shot peening. It was unexpectedly discovered that the drawbacks of shot-peening alone and swaging alone could be avoided when both of these surface conditioning techniques were combined. A shot-peening process immediately following the swaging process will impart residue compressive stresses on the surface, offsetting or canceling out the effect of unusual tensile stresses created by the swaging process. The compressive stress tends to pack surface grains together and exert pressure among different grains against each other. Consequently, the stress risers and pores are closed off and the outer surface is placed into organized uniformity. To eliminate the risk of stress corrosion cracking, the use of non-inert blasting media should be avoided. For this reason, inert glass shot-peening should be used in preference to steel shot-peening. To obtain a very controlled and repeatable level of peening on a production basis, the size range of the glass beads should be monitored and controlled. The recommended sieve ranges of glass beads for peening are 20–30, 30–40, and 40–60. Here, the glass shot-peening process serves primarily to refine the crystalline structure on the surface (rather than hardening). An additional desirable effect of glass shot peening is the clean appearance and decorative finish of the surface.

Swaging is a chipless machining operation. Neither the swaging technique nor the shot peening will etch or remove basic materials or impart any undesirable residues. The chemical composition of the basic material remains unchanged after the proposed manufacturing process. According to the AISI (the American Iron and Steel Institute) standard, the basic materials of the final product can still be classified as 304 stainless steel.

The swaging-peening process is simple to follow, and the dimensions can be precisely duplicated on an unlimited number of parts even when using operators with low levels of skill and experience.

The heat-transfer performance of vacuum brazed probes of the invention after the swaging-shot peening process closely resembles that of a standard probe, as presented in the following table. When tested in gel at room temperature, the difference in the performance between the swaged and non-swaged probes is more noticeable after extended freezing such as 15 minutes. The slight variation in probe performance, if any, might be attributable to the slight reduction in heat-transfer after swaging. The results of the study (see Table 1 below) also indicate that the performance of the probe starts to become severely degraded when the probe shaft is swaged to below 0.1275". To achieve the desired rigidity while ensuring the structural integrity of the probe, a probe shaft larger than 0.134", such as 0.135" or 0.136" may be used before swaging

TABLE 1

| | Cool-Down Time (Sec.) (n = 3) | Ice ball Size (after 15 min. Freezing in Water at 17° C.) (n = 3) | | | Minimum Temperature in Gel (°C.) |
|---|---|---|---|---|---|
| | | Dia. (mm) | Length (mm) | Weight (g) | |
| Standard Probe (0.132"–0.134") | 62.2 ± 4.7 | 30.7 ± 1.5 | 48.8 ± 1.3 | 20.8 ± 2.0 | −152 ± 29 (n = 4) |
| Swaged-Shot-Peened Probe (0.130") | 61.7 ± 9.7 | 29.4 ± 2.0 | 48.9 ± 1.8 | 19.4 ± 3.1 | −145 ± 28 (n = 5) |

To study the effect of the swaging-shot peening process on the rigidity and structural integrity of the probe shaft, different tests were conducted including bending moment, bending load, buckling load, tensile load (yield point), and bursting pressure.

The results are shown in the following Table 2.

TABLE 2

| | Bending Moment (in. lbs.) (n = 3) | | | | | Bending Load (Lbs) (n = 1) | Buckling Load (Lbs.) | Tensile Yield Load (Lbs.) | Bursting Pressure (psi) (n = 3) |
|---|---|---|---|---|---|---|---|---|---|
| | 10° | 20° | 30° | 40° | Ulti. | | | | |
| TIG-Welded (0.134") | 3.5 ± 0.2 | 6.8 ± 0.1 | 10.5 ± 0.1 | 15.1 ± 0.1 | 26.6 ± 0.4 | 28.1 | 83 ± 3.6 | 763 ± 78.9 | 9700 ± 1400 (C) |
| Swaged-Shot-Peened Probe (0.130") | 4.2 ± 0.0 | 7.0 ± 0.1 | 9.1 ± 0.1 | 10.0 ± 0.1 | 10.9 ± 0.1 | 14.2 | 80 ± 9.8 | 287 ± 14.8 | 8100 ± 0 (H) |
| Standard Probe (0.132"–0.134") | 3.5 ± 0.1 | 4.9 ± 0.1 | 5.4 ± 0.0 | 6.3 ± 0.1 | 6.8 ± 0.1 | 7.9 | 64 ± 6.5 | 200 ± 8.2 | 7233 ± 850 (C) |

Notes:
"C" and "H" denote respectively bursting at teflon connectors and handle of the probe In carrying out the method of this invention, the sub-assemblies and the final assembly are brazed in a vacuum brazing oven at a temperature of at least about 1000° F., preferably at least 1300° F., such as about 1500° F. or higher and at low pressure, i.e. at least as low as $1\times10^{-3}$ Torr. For example, for stainless steel parts using GB8218 brazing alloy brazing may be conducted at a temperature of about $1825^{+/-0}$° F. and at a pressure of about $1\times10^{-5}$ Torr. Generally, the sub-assemblies are assembled and brazed in batches, the number of sub-assemblies in each batch being limited primarily by the size of the oven. In the sub-assembly brazing procedure the sub-assemblies are loaded into the oven and a vacuum is drawn on the oven. The temperature in the oven is increased to the brazing temperature, for example, at a rate of about 30°–50° F. per minute. When the desired brazing temperature is reached, the furnace is held at that temperature for about 10–30 minutes depending on the mass of material in the furnace. Following brazing, the furnace temperature is reduced, usually at about the same rate as the temperature raising rate, such as about 30°–50° F. down to a temperature below the melting or softening temperature to a temperature below about 1300° F. At this point, the vacuum is released and the furnace is force cooled with dry nitrogen to a temperature of, for example, about 100° F. For brazing of final assemblies, the same procedure is followed with the exception that the temperature increase preferably occurs at a more gradual rate of, for example, about 10° F. per minute to ensure even heating of multiple layers. During brazing the sub-assemblies and final assembly are supported by fixtures preferably designed to hold a plurality of such assemblies and constructed of materials which can withstand the high temperatures and low pressures without adverse effect on the materials of the probes. A preferred material for these fixtures is graphite with a coating of boron nitrate.

Figure 20:
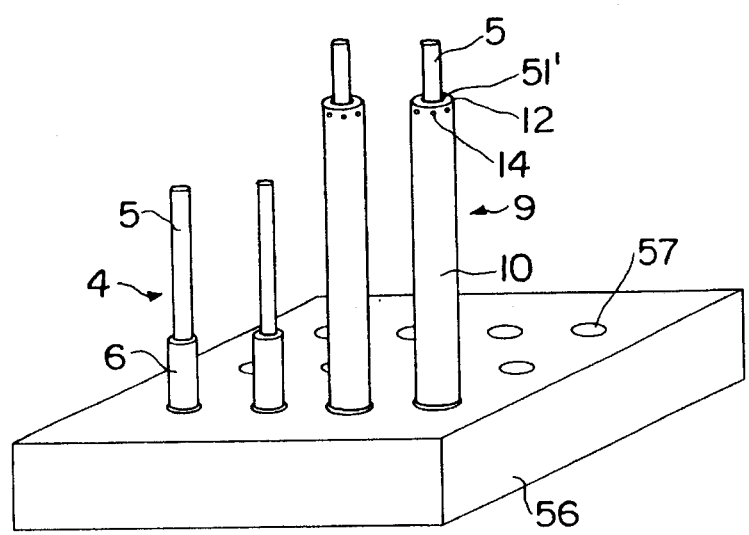
FIG. 20 is an oblique view of first and second subassemblies of the present invention supported for vacuum brazing.
Figure 19:
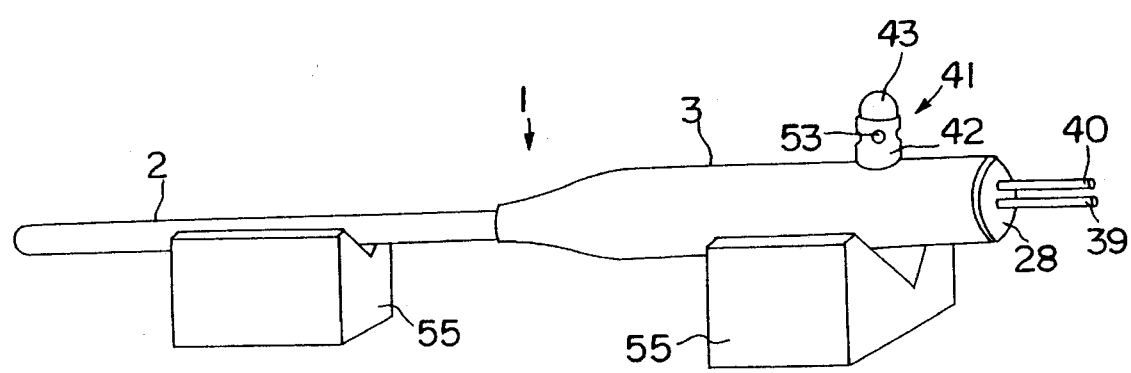
FIG. 19 is an oblique view of an individual cryosurgical probe assembly of the present invention supported for final vacuum brazing.

Preferably, the fixtures hold the sub-assemblies and final assemblies in a horizontal position. For this purpose the fixtures may be simple V-blocks 55, as shown in FIG. 19, of different heights to ensure that the probe assembly 1 is maintained in a level horizontal attitude or they may be specifically designed and fabricated with a configuration corresponding to the particular assemblies being vacuum brazed. In addition, the fixtures may be designed to be stackable, thereby providing multiple layers of assemblies in a stable arrangement. Alternatively, and particularly in the case of first sub-assemblies 4 and second sub-assemblies 9, the various assemblies may be supported vertically for vacuum brazing in blocks 56 having multiple apertures 57 in one surface into which the sub-assemblies are inserted as shown in FIG. 20. Vertical support of final probe assemblies is preferred when alternative valve body 242 and valve ball dispenser 156 are employed. Preferably, the design of the fixtures will permit a maximum number of sub-assemblies and/or final assemblies to be loaded into the furnace for each vacuum brazing operation.

A typical assembly of a probe according to the structure and method of the invention begins with first sub-assembly 4. Cryogenic fluid return tube 5 and connector tube 6 are assembled with a fill alloy brazing ring surrounding cryogenic fluid return tube 5 and pressed against proximal end 7 of connector tube 6. The fill alloy brazing ring may be about 0.083 inch in diameter which corresponds to the outside diameter of cryogenic fluid return tube 5. A plurality of first subassemblies 4 are loaded into a vacuum furnace which, between cycles, is maintained at a temperature of about 100° F. and a pressure of about $1\times10^{-3}$ Torr to remove condensation. Following loading, the furnace is closed, the pressure of about $1\times10^{-3}$ Torr is again established and the temperature is then increased to at least about 1500° F. and preferably to about 1700° F. to about 1750° F. at a rate of about 30°–50° F. per minute and then to about 1825° F. at a rate of about 5°–20° F. per minute. When a temperature of $1825^{+/-0}$° F. is reached it is held there for about 10–30 minutes, depending on the mass of material in the furnace. After brazing, the temperature of the furnace is reduced at a rate of 30°–50° F. per minute until about 1350° F. to about 1300° F. is reached at which time the vacuum is released and the furnace is force cooled with dry nitrogen to a temperature of about 100° F. and the first subassemblies 4 are removed and inspected. The furnace pressure may be reduced to about $1\times10^{-5}$ Torr for optimum brazing.

Second sub-assemblies 9 are assembled by placing a fill alloy brazing ring either in annular notch 11 of first sub-assembly 4, or over return tube 5 against connector tube 6, and then placing first sub-assembly 4 inside probe shaft 10. The fill alloy brazing ring may be about 0.083 inch in diameter to provide a snug fit of first sub-assembly 4 in probe shaft 10. At this point, the method permits easy adjustment of the size of freezing chamber 10' by varying the lengths and/or the extent to which first sub-assembly 4 is inserted into probe shaft 10. The assembled second sub-assemblies 9 are vacuum brazed in one brazing cycle as described for first sub-assemblies and are then vacuum tested to ensure a good seal between connector tube 6 and probe shaft 10.

Third sub-assemblies 15 are assembled from second sub-assemblies 9, return tube extension 16, chamber body 17 and spacer 18 with spacer 18 being placed within proximal end 12 of probe shaft 10 and proximal end 12 of probe shaft 10 being crimped to hold spacer 18 in place. However, preferably, locking wire 18' is threaded through adjacent vent holes 14 before spacer 18 is applied to thereby prevent passage of spacer 18 into probe shaft 10 beyond vent holes 14. In this manner, proximal end 12 of probe shaft 10 need not be crimped. It is particularly preferred that spacer 18 have a reasonably snug fit within probe shaft 10. Alternatively, spacer 18 may be installed when second sub-assemblies 9 are assembled and may also be vacuum brazed in place at that step. A fill alloy brazing ring which may be about 0.083 inch diameter is placed over cryogenic fluid return tube 5 and against distal end 19 of return tube extension 16 and a fill alloy brazing ring of about 0.156 inch diameter, which corresponds to the outside diameter of return tube extension 16, is placed around return tube extension 16 and within bore chamfer 23 on chamber body 17. Third sub-assemblies 15 are brazed as described and visually inspected then set aside for use in assembling final probe assemblies 1.

Fourth sub-assemblies 25 are assembled from cryogenic fluid supply tube 26, supply tube extension 27 and end cap 28. If desired, thermocouple well 37 is also assembled to end cap 28. At this time, cryogenic fluid supply connector 39 and cryogenic fluid return connector 40 may be assembled to end cap 28 or they may be reserved until final assembly. Fill alloy brazing rings are positioned at appropriate locations, notably a ring of about 0.042 inch diameter, corresponding to the outside diameter of cryogenic fluid supply tube 26, is placed over cryogenic fluid supply tube 26 and against distal end 29 of supply tube extension 27 and a ring of about 0.083 inch diameter, corresponding to the outside diameter of supply tube extension 27, is placed over supply tube extension 27 to fit in chamfer 33 of end cap central bore 30. Fourth sub-assemblies are processed in one brazing cycle as described and the joints are visually inspected.

In the final assembly of probe 1, fourth sub-assembly 25 is assembled to third sub-assembly 15 by insertion of cryogenic fluid supply tube 26 and supply tube extension 27 into cryogenic fluid return tube 5 and return tube extension 16. End cap 28 is placed against circumferential chamfered edge 35 of chamber body 17 so that edge 35 engages circumferential shoulder 34 of end cap 28. The mating edge 35 and shoulder 34 preferably cooperate to form an annular notch which accommodates a fill alloy brazing ring of about 0.875 inch diameter. A further fill alloy brazing ring of about 0.625 inch diameter is positioned in annular notch 24' of annular shoulder 24 and handle body 38 is placed over third sub-assembly 15. Annular shoulder 24 and the fill alloy brazing ring in notch 24' are received within proximal end 46 of handle body 38, as shown in FIG. 8, and a fill alloy brazing ring of about 0.134 inch diameter, corresponding to the diameter of probe shaft 10, is placed over probe shaft 10 against necked distal end 49 of handle body 38. Alternatively, proximal end 46 of handle body 38 is brazed to chamber wall 21 by means of a fill alloy brazing ring placed over handle body 38 and against chamber wall 21 rather than in notch 24'. If they were not included in the assembly of fourth sub-assembly 25, cryogenic fluid supply and return connectors 39 and 40 are installed at this time with fill alloy brazing rings of about 0.097 inch diameter positioned thereon against end cap 28. The final assemblies are positioned with valve body 42 uppermost and getter 54 is introduced into handle space 51 through valve body 42. A fill alloy brazing ring of about 0.295 inch diameter, corresponding to the diameter of valve body 42, is used to braze valve body 42 to handle body 38 and a brazing ring of about 0.257 inch diameter, i.e., the diameter of seat 52, is placed on seat 52. Activation wire 44 and ball 43, if not preassembled, are installed on valve body 42 and the final assemblies are loaded into the furnace for brazing. If valve body 242 is employed, it is placed in valve hole 47 with an appropriate fill alloy brazing ring. Valve ball dispenser 156 is attached to probe 1 and the entire assembly is supported vertically, as shown in FIGS. 21 and 22, within the furnace.

In the brazing procedure for final assemblies 1, the furnace is loaded and evacuated to at least $1 \times 10^{-3}$ Torr, preferably about $1 \times 10^{-5}$ Torr. Evacuation at this stage serves a two-fold purpose. In addition to preparing the furnace for brazing, evacuation also draws a vacuum on handle space 51 through valve 41 and on coaxial lumen 51' which communicates with handle space 51 through vents 14. Vents 53 in valve body 42 communicate with handle space 51 through valve body 42. Following evacuation, the thermal schedule as previously described is applied. Preferably, however, the furnace temperature is increased to at least 1500° F., and preferably to about $1825^{+30}/_{-0}$° F. at a rate of about 10° F. per minute. At brazing temperature, activation wire 44 melts allowing ball 43 to fall into valve body 42 onto seat 52 where the fill alloy brazing ring applied to seat 52 during assembly fuses ball 43 to seat 52 thereby closing valve 41. In this manner, handle space 51 and coaxial lumen 51' are sealed and the vacuum therein is maintained following brazing thereby providing an evacuated insulating layer which extends for substantially the entire length of probe assembly 1 except for freezing chamber 10' at probe tip 13. As with the brazing procedure for the sub-assemblies, the brazing temperature is held for about 10–30 minutes then decreased at a rate of about 30°–50° F. per minute to about 1300°–1350° F. at which point the furnace vacuum is released and the furnace is force cooled to 100° F. with dry nitrogen.

All parts are pre-cleaned before assembly and brazing to remove any dirt, oils, grease or other materials which could interfere with the brazing process or form contaminants in the finished probes. Solvents appropriate to the materials used may be employed; however, a preferred pre-cleaning procedure is to clean the parts by vapor degreasing using a solvent such as Genusolv 54/33 in a Branson three-phase system where phase 1 is a boiling phase, phase 2 is a vapor phase, and phase 3 is an ultrasonic cleaning phase.

An alternative construction embodiment of the probe of this invention is illustrated in FIGS. 12–17. Principally, this embodiment is a probe according to the present invention wherein chamber body 17 and cryogenic fluid return chamber 48 have been incorporated as part of return tube extension 16. The result is a sleeker, more streamlined probe 100 as shown in FIG. 12.

In this embodiment, the construction of first sub-assembly 104 is substantially identical to that of the first embodiment with connector tube 106, having notch 111 for receiving a brazing ring, being joined to cryogenic fluid return tube 105. In second sub-assembly 109, probe shaft 110, including closed end 113 forming the probe tip, is placed over first sub-assembly 104 and vacuum brazing is carried out as previously described. As in the first embodiment, a short portion of the proximal end of the return tube 105 will protrude from the open proximal end of the probe shaft 110.

In third sub-assembly 115, locking wire 118' is threaded through adjacent vent holes 114 and spacer 118 is placed over return tube 105 within proximal end of probe shaft 110. Return tube extension 116 is joined to cryogenic fluid return tube 105 as in the first embodiment. However, the structure of return tube extension 116 is different. Return tube extension 116 is formed with a larger diameter along its entire length, distal end 119 being tapered down to join cryogenic fluid return tube 105. The effect is to increase the volume of that portion of cryogenic fluid return lumen 150 between return tube extension 116 and supply tube extension 127 as seen in FIGS. 12 and 14. This portion of lumen 150 then also serves as the cryogenic fluid return chamber 48 of the first embodiment.

Figure 5B:
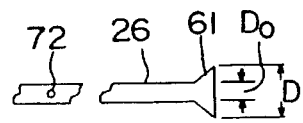
FIG. 5b is a detail view of the discharge end of a cryogenic fluid supply tube having a diverging nozzle.
Figure 5A:
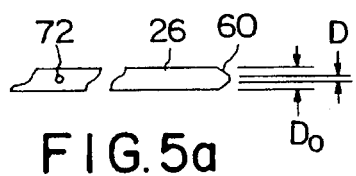
FIG. 5a is a detail view of the discharge end of a cryogenic fluid supply tube having a converging nozzle.

Fourth sub-assembly 125 is also substantially identical to fourth sub-assembly 25 of the first embodiment and comprises cryogenic fluid supply tube 126, supply tube extension 127 and end cap 128 which are joined by vacuum brazing. Supply tube vent holes 170 and 172 are located along the length of the supply tube 126 and supply tube extension 127. Supply tube 126 may also be formed with a converging nozzle 60 or a diverging nozzle 61 as shown in FIGS. 5a and 5b. The design of end cap 128 is modified to accommodate the alternative construction of this embodiment as shown in FIGS. 15 and 16 and incorporates features of chamber body 17. As shown, end cap 128 includes end cap central bore 130 and first radial offset bore 131, supply tube extension 127 being joined to end cap central bore 130 while first offset bore 131 provides access to lumen 150 for cryogenic fluid return connector 140. Cryogenic fluid supply connector 139 joins to end cap central bore 130. Circumferential shoulder 134 provides a mating surface for proximal end 146 of handle body 138. Annular shoulder 124 corresponds to annular shoulder 24 of the first embodiment and fits in proximal end 146 of handle body 138 in a similar plug like manner. Within annular shoulder 124 is a central end cap recess 122 which corresponds to bore 22 of chamber body 17 and in which proximal end 120 of return tube extension 116 fits upon final assembly. End cap recess 122 is bounded by wall 122' and encompasses end cap central bore 130 and first radial offset end cap bore 131.

Figure 18:
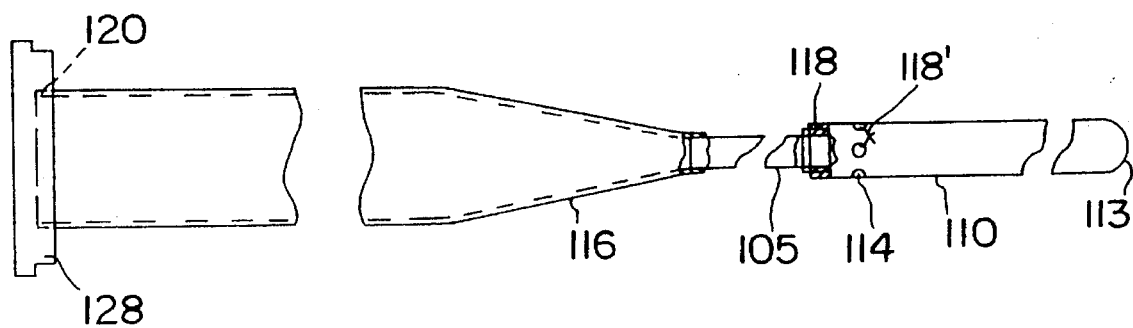
FIG. 18 is a plan view of the probe of FIG. 12 with the handle body removed.

FIG. 18 shows a partial final assembly with end cap 128 in place on proximal end 120 of return tube extension 116. Vents 114 in probe shaft 110 correspond to vents 14 in the first embodiment and serve to provide communication between handle space 151 and coaxial lumen 151' (see FIG. 13) for evacuation during the final vacuum brazing step of this embodiment. As in the first embodiment, when probe 100 is completely assembled, vents 114 will be proximal to necked end 149 of handle body 138 and will, therefor, be within handle space 151.

Figure 17:
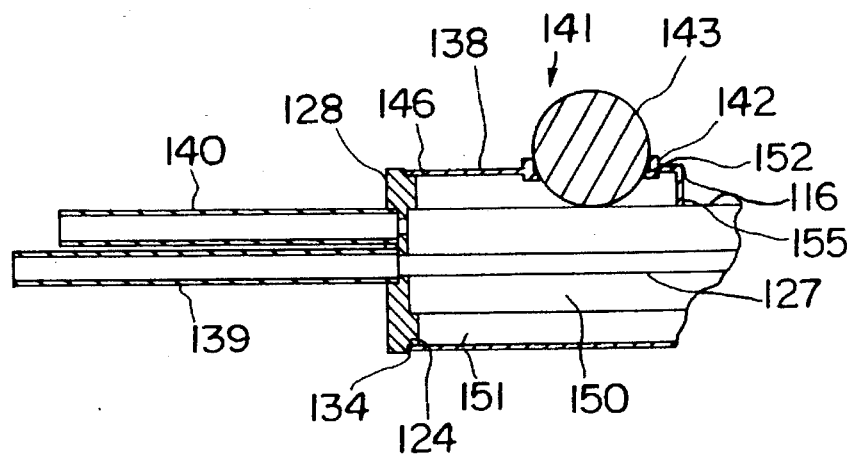
FIG. 17 is a detail view of area C of FIG. 12.

FIG. 17 shows a detail cross section of the assembly with handle body 138 in place and valve ball 143 sealed to valve seat 152 in valve body 142. As in the first embodiment, getter pills 154 are inserted through valve 141 prior to final brazing. In order to confine getter pills 154 within the proximal end of probe 100, mesh screen 155 is positioned distally of valve 141 between return tube extension 116 and handle body 138. The subassemblies and the final assembly may be brazed in the same manner as described for the first embodiment.

In a further modification of the second embodiment, return tube extension 116 may be assembled to cryogenic fluid return tube 105 as part of first sub-assembly 104 thus eliminating the third sub-assembly step. In that instance, spacer 118 and a fill alloy brazing ring are pre-positioned on return tube 105 before return tube extension 116 is added and this assembly is inserted into probe shaft 110 a sufficient distance for connector tube 106 to pass vent holes 114 at which point locking wire 118' is installed and the sub-assembly is completed.

The probe constructions and method of this invention eliminate the need for separate and complicated evacuation procedures which have been previously necessary to achieve thermal insulation of probe handles. In addition, the overall construction produces a probe with reduced flow resistance over prior welded or press-fit constructions. Furthermore, since vacuum brazing is a fluxless process and substitutes the vacuum for mineral fluxes used in other methods, more uniform joints are obtained and the vacuum insulation is less susceptible to degradation. Because fluxes are not used, the cryoprobes of the invention experience a minimum of base-metal outgassing which, in prior constructions, degrades the joints. Accordingly, the present invention results in longer shelf life periods for the probes produced.

Since multiple assemblies can be loaded into a furnace and vacuum brazed at the same time, the method of this invention is suitable for high volume production operations and results in high quality probes with high uniformity and consistency. Accordingly, the method of this invention is more economical in terms of labor and materials and produces greater numbers of probes at lower cost thereby justifying disposability of the probes after use and eliminating defects that appear as the result of reuse.

At this point, it is again noted that the vacuum brazing method presented herein contributes to a particularly desirable feature of the probes of the invention. Although the probes may be produced with the probe portion perfectly straight, occasions arise where it is convenient to provide a curved probe shaft. The slow cooling of the furnace from brazing temperature to about 1300° F. or below provides an annealing process which results in increased flexibility of the probe shaft portion allowing the shaft to be bent to a particular shape yet retain sufficient rigidity to hold that shape until re-bent. Alternatively, the probe portion may be bent to a particular shape during assembly then heat treated to fix the bend angle. Such treatment is a function of the vacuum brazing process and is accomplished by adjusting the cool down step to provide annealing or tempering of the probe material. Thus, if a stiffer probe is desired, a faster cool down step is used to temper the material. Alternatively, a slower cool down will increase probe flexibility as the result of annealing the probe material. This flexibility in construction and properties of the probes is a direct result of using the vacuum brazing process and is obtained without affecting either the structural integrity of the probes or the flow characteristics of the cryogenic fluid through the probe.

Moreover, as described above, by using lower melting temperature brazing alloys, it is possible to avoid heating the probe materials to temperatures which will result in softening and recrystallization. Furthermore, where additional hardening is desirable, any of the methods described previously may be applied to the probe shaft or other elements of the probe. In particular, the combined swaging and shot-peening process described above may be advantageously applied to the probe shaft, particularly those probe shafts having diameters below about 5 millimeters, such as about 3 or 4 millimeters.

Figure 23:
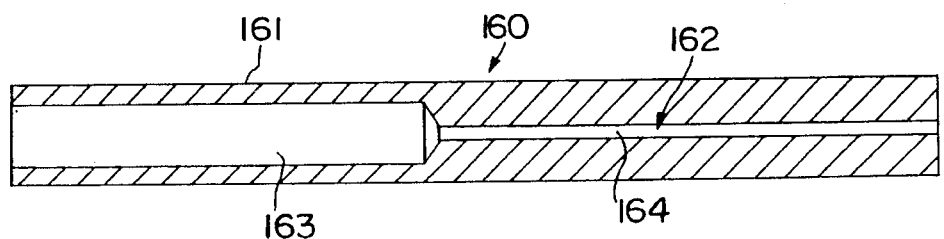
FIG. 23 is a longitudinal cross section of a tubular probe shaft straightening tool for use in the manufacture of a cryosurgical probe of the present invention.
Figure 24:
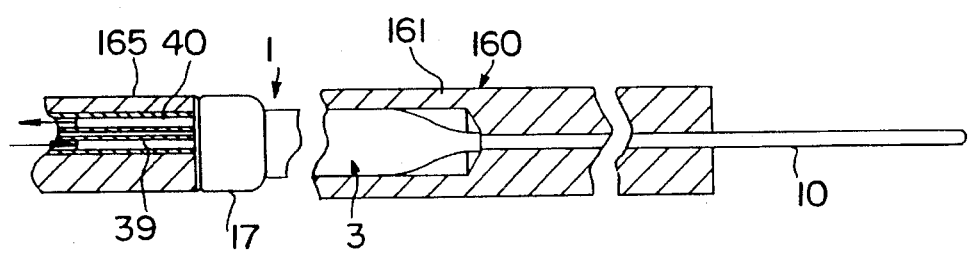
FIG. 24 is a longitudinal cross section of the probe shaft straightening tool of FIG. 23 in place on a probe of the present invention.

The present invention also provides a method for straightening probes which become bent during manufacture or use and which makes use of a relatively simple apparatus which is illustrated in FIGS. 23 and 24. Probe shaft tool 160 comprises an elongated block of rigid material, preferably stainless steel, which has a centrally disposed bore 162 extending longitudinally through block 161. Longitudinal bore 162 is divided into probe cavity 163, which has a diameter sufficient to receive handle portions 3 and 103 of probes 1 and 100, and a shaft channel 164, which has a diameter sufficient to receive probe portions 2 and 102 of probes 1 and 100. Preferably, the diameter of shaft channel 164 is just large enough to permit a straight probe portion to pass through and will thereby exert a straightening effect on a curved or bent probe which is inserted therein. In addition, probe shaft tool 160 is preferably of a length to permit substantially the full length of probe portions 2 and 102 to be received in shaft channel 164. Where it is desired to provide a particular curvature to probe portions 2 and 102, tool 160 may be provided with a curved shaft channel 164 so that probe portions 2 and 102 will bend to that curvature when they are inserted.

In the procedure for straightening or curving probes using shaft tool 160, tool 160 is placed over probes 1 or 100 so that handle portion 3 or 103 is received within probe cavity 163 and probe portions 2 or 102 extend through shaft channel 164 as shown in FIG. 24. Liquid nitrogen, or other cryogenic fluid, is provided to probe 1 or 100 through cryogenic fluid hose 165 and is circulated through probe 1 or 100 for about 3–5 minutes. Flow of cryogenic fluid is then stopped and the probe is allowed to warm until frost melts at which time tool 160 is removed. The cooling and warming of the probe while tool 160 is in place facilitates retention of the set given to the probe shaft by tool 160.

The design of the probes and their method of manufacture also contribute to safety and versatility. Since there are fewer joints and the annealing or tempering effect of brazing renders them stress free, the probes withstand thermal shock with higher reliability and consistency. In addition, no welded joints are exposed for possible contact with the patient. Versatility is improved due to the method of construction which permits ready variation in the length of the freezing chamber which allows the actual freezing area of the tip to be easily changed during construction to provide probes which will produce different size ice balls. In addition, the compact design permits multiple probes to be positioned in a limited surgical area.

As noted above, vacuum brazed cryoprobes have many advantages over conventional cryoprobes of the same or similar design but wherein the various parts are connected by other welding or brazing techniques. However, in connection with the assignee's Tig-welded, supply tube vented cryoprobes, and most notably those with small diameter probe shafts, e.g. 3 millimeter cryoprobes, of the type described in the aforementioned U.S. Pat. No. 5,254,116 and copending application Ser. No. 08/137,353, it was discovered in laboratory tests that the external tip temperatures at the same cryogen (liquid nitrogen) flow rates and pressures and the same vent hole design were up to about 40° C. higher in the vacuum brazed cryoprobe of this invention than in the Tig-welded cryoprobes.

Further studies have shown that the external probe tip temperature could be lowered to that achieved with the Tig-welded cryoprobes (about −140° C. or lower) and in substantially the same time periods, e.g. within about 20 minutes, preferably within about 15 minutes, by providing a nozzle at the supply tube outlet (discharge end). Further optimization is achieved by the configuration of the supply tube vent hole design (number of holes, location of holes, diameter of holes, etc.).

The nozzle may be either converging, i.e. (D-Do)/Do<0, where D is the nominal inner diameter of the nozzle and Do is the nominal inner diameter of the regular supply tube (e.g. 0.035 inch in a 3 millimeter cryoprobe), or diverging, i.e. (D-Do)/Do>0. A supply tube with a converging nozzle 60 at its discharge end is shown in FIG. 5*a* and a supply tube with a diverging nozzle 61 at its discharge end is shown in FIG. 5*b*. The nozzles may be formed by any conventional technique, such as with a tapered tool of appropriate dimensions.

An especially preferred design enabling external tip temperatures of as low as about −140° C. or lower within from 10 to 15 minutes, using a nominal 3 mm (e.g. 3.4 mm) vacuum brazed probe (i.e. probe shaft) of about 15 inches total length (including cryogenic fluid supply connector 39), and a supply tube of about 13.4 inches (total length), with liquid nitrogen (LN$_2$) refrigerant (at 55 psi supply pressure), is achieved for a cryoprobe as shown in FIGS. 1–8 with a converging nozzle having a diameter reduction of from about 12% (D=0.031", Do=0.035") to about 22% (D=0.027", D=0.035") and a vent hole design which includes one large diameter (about 0.027") vent hole (70) in enlarged chamber 48 and four smaller (about 0.007" diameter) vent holes (72). The four smaller vent holes 72 may be equi-spaced along supply tube 26 and extension 27, starting, for example, at about 0.5 inch to 1.0 inch from the discharge end of the supply tube and extending to about 8 to 10 inches from the discharge end, such that one small hole 72 is located in extension 27 and three are located in supply tube 26. Alternatively, the three vent holes 72 located in supply tube 26 may be located within about 0.5 inch to 0.6 inch, 0.75 to 0.9 inch, and 1.0 to 1.2 inch, respectively, from the discharge end, such that the forwardmost hole is located within the freeze zone (i.e. distally of the vacuum insulation), the intermediate hole is located at or near the inlet to the cryogenic fluid return lumen 50, and the rearmost hole is located within the cryogenic fluid return lumen 50. In each case the fourth vent hole 72 is located in supply tube connector 27 forwardly of (i.e. downstream) chamber body 17 and enlarged return chamber 48.

The foregoing description sets forth the preferred construction and method of the present invention. Variations and modifications which would be evident to one of ordinary skill and knowledge are considered to be included herein and within the scope of the appended claims.

What is claimed is:

1. A method of manufacturing a cryogenic surgical probe instrument having an elongated probe shaft portion, an evacuated handle portion and means for connecting said instrument to a supply of cryogenic fluid, said method comprising a) providing individual parts of said instrument formed from brazable material, b) assembling said parts into said cryogenic surgical probe instrument, c) applying brazing alloy to the junctions where said parts are to be joined, and d) vacuum brazing said assembled parts at reduced pressure and at a temperature sufficient to melt said brazing alloy and promote fluxless brazing whereby said parts are fused together to complete said instrument and said handle portion and a portion of said probe shaft portion are simultaneously evacuated and sealed.

2. The method of claim 1 further comprising the steps of assembling selected parts into sub-assemblies and brazing said sub-assemblies at reduced pressure and at temperature sufficient to melt said brazing alloy and promote fluxless brazing for a period of time to complete said brazing, followed by assembly of said sub-assemblies into a final assembly corresponding to said cryogenic surgical probe instrument and brazing said final assembly at reduced pressure to evacuate said handle portion and said probe portion and at temperature sufficient to melt said brazing alloy and promote fluxless brazing for a period of time to complete said brazing.

3. The method of claim 2 wherein each of said brazing steps is conducted under reduced pressure in a brazing furnace in a cycle comprising the steps of:

a) placing said assemblies in said furnace, b) evacuating said furnace to a reduced pressure of at most about $1 \times 10^{-3}$ Torr, c) increasing the temperature of said furnace to at least the brazing temperature of the brazable material at a rate of about 30° to 50° F./minute, d) holding said at least brazing temperature for a period of from about 10 to about 30 minutes, e) decreasing said temperature to a temperature below the softening temperature of the brazable material at a rate of about 30° to 50° F./minute, and f) releasing said vacuum and force cooling said furnace with dry nitrogen to a temperature of about 100° F.

4. The method of claim 3 wherein said brazable material is a medical grade stainless steel and wherein said furnace is evacuated to a reduced pressure of about $1 \times 10^{-5}$ Torr and in step c) said temperature is increased to and held at about 1825° F.

5. The method of claim 3 wherein the rate of temperature decrease in step e) during brazing of said final assembly is regulated to produce an annealing effect whereby the flexibility of said elongated probe portion is increased.

6. The method of claim 3 wherein the rate of temperature decrease in step e) during brazing of said final assembly is regulated to produce a tempering effect whereby the flexibility of said elongated probe portion is reduced.

7. The method of claim 3 wherein the probe portion of said final assembly is formed to a desired shape prior to brazing and whereby said brazing at reduced pressure and elevated temperature sets the shape of said probe portion.

8. The method of claim 2 further comprising providing a thermally activatable valve in the handle portion of said final assembly, evacuating at least said instrument handle portion during said vacuum brazing and thermally activating said thermally activatable valve whereby upon vacuum brazing of said final assembly a vacuum is applied to and maintained in said handle portion and a portion of said probe shaft portion of said instrument.

9. The method of claim 1 wherein in step b) said parts are assembled with a tolerance to provide a gap just sufficient to allow gaseous substances within at least said handle portion and a portion of said probe shaft portion to be evacuated during vacuum brazing.

10. A method of manufacturing a cryogenic probe having a distal closed tip probe shaft portion and proximal connection means to a supply of cryogenic fluid, the method comprising:

a) providing a first sub-assembly comprising a cryogenic fluid return tube and a connector tube in linear arrangement and vacuum brazing said first sub-assembly whereby the proximal end of said connector tube is joined to the distal end of said cryogenic fluid return tube, b) telescopically positioning an elongated tubular tip having a closed distal end and an open proximal end with apertures adjacent said proximal end over said first sub-assembly whereby said connector tube is fully contained within said tubular tip and the proximal end of said cryogenic fluid return tube extends from the proximal end of said tubular tip and vacuum brazing said tubular tip to said first sub-assembly whereby a second sub-assembly is formed, c) aligning a cryogenic fluid return assembly comprising (1) a substantially cup shaped cryogen chamber having an open proximal end and an apertured base and (2) an extension tube extending axially from the aperture in said base and connectable to the proximal end of said cryogenic fluid return tube of said first sub-assembly with the longitudinal axis of said second sub-assembly and vacuum brazing said cryogen chamber to said extension tube and said extension tube to said cryogenic fluid return tube whereby a third sub-assembly is formed, d) forming a fourth sub-assembly comprising (1) an end cap adapted to engage and seal the open end of said substantially cup shaped cryogen chamber, said end cap having an inner and an outer surface, a central supply aperture extending from said inner surface to said outer surface and a radially offset return aperture extending from said inner surface to said outer surface, and (2) a cryogenic fluid supply tube extending perpendicularly from said central supply aperture on said inner surface of said cap by vacuum brazing said cap and said supply tube together, and e) conducting final assembly of said cryogenic probe by (i) inserting said third sub-assembly into a tubular handle body having a thermally activatable valve in a wall thereof whereby the distal end of said third sub-assembly extends through and beyond the distal end of said handle body with said apertures adjacent to the proximal end of said elongated tip being located within said handle body whereby the area within said handle body communicates with the area within said probe portion and whereby the proximal end of said handle body engages the base of said cryogen chamber, (ii) inserting said fourth sub-assembly into said third sub-assembly whereby said cryogenic fluid supply tube extends telescopically into said cryogenic fluid return tube and said end cap engages and closes the proximal end of said cryogen chamber, and vacuum brazing said cryogenic probe to join said third and fourth sub-assemblies to said handle body;

whereby during vacuum brazing in step e) the handle body and the probe portion are evacuated via said thermally activatable valve, and said valve is thermally activated and sealed whereby a vacuum drawn in said handle body and said probe portion is maintained upon and following completion of brazing.

11. The method of claim 10 which comprises simultaneously vacuum brazing a plurality of assemblies whereby a plurality of said probes are simultaneously manufactured.

12. The method of claim 10 wherein brazing is conducted at a temperature of at least about 1000° F. and a reduced pressure of at most about $1 \times 10^{-3}$ Torr.

13. The method of claim 12 wherein said brazing is conducted at a vacuum of about $1 \times 10^{-5}$ Torr and a temperature of at least about 1300° F.

14. In a cryogenic probe comprising an elongated handle portion, a probe shaft portion extending from one end of said handle portion, said probe shaft portion having a closed tip at the distal end thereof, cryogenic fluid connection means on said handle portion, cryogenic supply and return tubes longitudinally coaxial within said handle portion and said shaft portion and extending to said closed probe tip, said handle portion and said shaft portion defining a space about said cryogenic supply and return tubes, the distal end of said shaft being sealed from said space, and said cryogenic fluid connection means and said cryogenic supply and return tubes forming a fluid circuit extending through said handle portion and said probe shaft, the improvement comprising;

said parts forming said probe being fluid tightly and smoothly joined by vacuum brazing.

15. A method of manufacturing a cryogenic probe having an elongated probe shaft portion extending longitudinally from an elongated handle portion and having concentric cryogenic fluid supply and return conduits passing through said handle portion into said probe shaft portion, whereby said supply conduit is within and terminates distally of said return conduit and said handle portion and said probe shaft portion are simultaneously evacuated and sealed, the method comprising:

a) providing said probe shaft portion comprising a first sub-assembly comprising an elongated tubular probe shaft having a closed distal end and an open proximal end and an elongated cryogenic fluid return tube extending telescopically within said probe tip and vacuum brazing said first sub-assembly, b) providing a second sub-assembly comprising said first sub-assembly and a return tube extension connected to the proximal end of said return tube in axial alignment with said first sub-assembly and vacuum brazing said return tube extension to said return tube, c) providing a third sub-assembly comprising a cryogenic fluid supply tube, a supply tube extension connected to the proximal end of said supply tube in axial alignment therewith and an end cap connected to the proximal end of said supply tube extension and vacuum brazing said third sub-assembly, d) providing an elongated tubular handle body and assembling said handle body and said sub-assemblies into a final assembly by inserting said second sub-assembly into said handle body whereby said probe portion extends from a distal end of said handle body and said return tube extension is confined within said handle body, inserting said third sub-assembly into said second sub-assembly whereby said cryogenic fluid supply tube extends telescopically into said return tube, said supply tube extension is confined within said return tube extension and said end cap closes the proximal end of said return tube extension and the proximal end of said handle body, and vacuum brazing said final assembly whereby said handle body and said probe portion are evacuated and the distal end of said handle body is fused to said probe shaft portion and said end cap is fused to said proximal ends of said return tube extension and said housing body thereby sealing said probe to maintain a vacuum therein.

16. The method of claim 15 further comprising providing, in said third sub-assembly, cryogenic fluid supply and return connectors extending proximally from said end cap and respectively connecting to said supply tube extension and to said return tube extension.

17. The method of claim 16 further comprising providing a thermally activatable valve in said handle body whereby during vacuum brazing of said final assembly in step d) a vacuum is drawn in said handle body and said probe shaft portion between said handle body and said return tube extension and between said probe shaft and said return tube and thermally activating said valve whereby said valve is sealed during said vacuum brazing thereby maintaining said vacuum in said handle body and said probe portion.

18. The method of claim 17 wherein vacuum brazing is performed at a temperature of at least 1300° F. and a reduced pressure of at most $1 \times 10^{-3}$ Torr.

19. The method of claim 16 wherein in step d) the steps of forming said final assembly comprises inserting said second sub-assembly into said handle body and inserting said third sub-assembly into said second sub-assembly under tolerance conditions which provide a small gap sufficient to allow gaseous substances within said final assembly to be evacuated from said final assembly during vacuum brazing thereof, and vacuum brazing said final assembly.

20. A cryogenic surgical probe comprising a probe shaft portion and a handle portion, said probe portion comprising, in concentric arrangement, an inner elongated cryogenic fluid supply tube, an intermediate elongated cryogenic fluid return tube and an outer elongated probe shaft wherein said probe shaft has a closed distal end and an open proximal end, said cryogenic fluid return tube terminates proximally of the closed distal end of the probe shaft and said cryogenic fluid supply tube terminates intermediate the distal ends of said return tube and said probe shaft, said handle portion having a diameter greater than said probe portion and comprising, in concentric arrangement, an inner supply tube extension, an intermediate return tube extension and an outer handle body;

wherein said handle portion is in longitudinal alignment with said probe shaft portion, said supply tube extension connects to the proximal end of said cryogenic fluid supply tube, said return tube extension connects to the proximal end of said cryogenic fluid return tube and said handle body connects to the proximal end of said probe shaft and wherein the proximal end of said handle portion is closed by an end plate having first and second cryogenic fluid connection tubes extending therethrough whereby said probe is connectable to a source of cryogenic fluid, said first connection tube connecting to said supply tube extension and said second connection tube connecting to said return tube extension, and wherein all of said connections are fused by vacuum brazing.

21. The cryogenic probe of claim 20 further comprising a thermally activated valve in said handle portion whereby the vacuum drawn within said handle portion and said probe shaft portion by said vacuum brazing via said valve is sealed by brazing to thereby maintain said vacuum in said handle portion and said probe portion.

22. The cryogenic surgical probe of claim 20 further comprising a connector tube fitted at one end thereof over the distal end of the cryogenic fluid return tube and at the other end thereof fitted within the proximal end of said probe shaft and extending thereinto; a lumen between said cryogenic fluid return tube and said probe shaft proximal of said connector tube; a spacer positioned over said cryogenic fluid return tube within the proximal end of said probe shaft; and, at least one aperture in said probe shaft, with said at least one aperture at a location distally adjacent to said spacer and wherein said distal end of said handle body is joined to said probe shaft distally of said apertures whereby said apertures provide communication between said handle portion and laid lumen between said probe shaft and said cryogenic fluid return tube.

23. The cryogenic surgical probe of claim 22 further comprising a thermally activated thermally activatable valve in said handle portion whereby the vacuum drawn within said handle portion and within said lumen by way of said apertures in said probe shaft and said valve is sealed by brazing to thereby maintain said vacuum in said handle portion and said lumen.

24. The method of claim 1 further comprising increasing the hardness of the probe shaft portion by subjecting the elongated probe shaft portion to swaging to decrease the diameter thereof and thereafter subjecting the swaged probe shaft portion to shot-peening with inert blasting media.

25. The method of claim 1 wherein prior to swaging the elongated shaft portion has a diameter in the range of from 0.132 to 0.134 inch and after swaging the diameter is decreased to 0.130 inch.

26. The cryogenic probe of claim 14 wherein said probe shaft portion has been hardened by a combination of swaging and shot-peening.

* * * * *